United States Patent [19]

Frazer et al.

[11] 4,451,642
[45] May 29, 1984

[54] BIS(AMINONEOPENTYL) AROMATICS AND POLYAMIDES DERIVED THEREFROM

[75] Inventors: August H. Frazer; John F. Harris, Jr., both of Wilmington, Del.

[73] Assignee: E. I. Du Pont de Nemours and Company, Wilmington, Del.

[21] Appl. No.: 420,511

[22] Filed: Sep. 20, 1982

Related U.S. Application Data

[60] Division of Ser. No. 266,058, May 21, 1981, which is a continuation-in-part of Ser. No. 804,853, Jun. 8, 1977, abandoned.

[51] Int. Cl.$^3$ .............................................. C08G 69/26
[52] U.S. Cl. ................................... 528/347; 528/344; 528/348; 528/349; 528/370; 528/372
[58] Field of Search ................ 528/349, 348, 347, 344

[56] References Cited

U.S. PATENT DOCUMENTS

| | | | |
|---|---|---|---|
| 2,464,693 | 3/1949 | Kirk et al. | 260/78 |
| 2,497,673 | 2/1950 | Kirk | 260/515 |
| 2,891,088 | 6/1959 | Condo et al. | 260/456 |
| 2,900,369 | 8/1959 | Edwards et al. | 260/78 |
| 3,175,007 | 3/1965 | Berhenke | 260/571 |
| 3,388,103 | 6/1968 | Imohl et al. | 260/77.5 |
| 3,422,143 | 1/1969 | Bottomley | 260/570.8 |
| 3,776,890 | 12/1973 | Lee | 260/78 R |

FOREIGN PATENT DOCUMENTS 799762 8/1958 United Kingdom .
938787 10/1963 United Kingdom .

OTHER PUBLICATIONS

J. Polymer Science, Stephens, vol. XL, pp. 359–366 (1959).
Synthetic Organic Chemistry, Wagner & Zook, Wiley 1953, p. 591.

*Primary Examiner*—Harold D. Anderson
*Attorney, Agent, or Firm*—James A. Costello

[57] ABSTRACT

Aromatic-aliphatic diamines of the formula

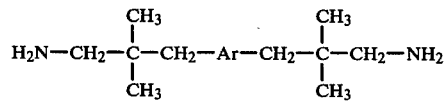

in which Ar is an arylene or substituted arylene are useful in preparing thermally stable, rigid, polyamides, polyureas and polyurethanes having a repeating unit of the formula

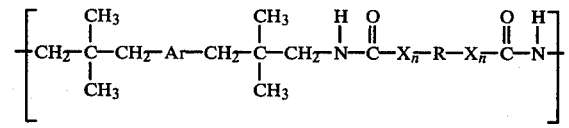

in which Ar is arylene or substituted arylene, X is —NH— or —O—, n is 0 or 1, and R is a divalent organic radical. Polymers of this invention can be melt-spun into thermally stable fibers.

3 Claims, No Drawings

BIS(AMINONEOPENTYL) AROMATICS AND POLYAMIDES DERIVED THEREFROM

CROSS-REFERENCE TO RELATED APPLICATIONS

This is a divisional application of copending application bearing U.S. Ser. No. 266,058, filed on May 21, 1981, which is a continuation-in-part of application bearing U.S. Ser. No. 804,853, filed June 8, 1977 and, now abandoned.

BACKGROUND OF THE INVENTION

1. Field of the Invention

This invention relates to aliphatic diamines, and more particularly to aromatic-aliphatic diamines containing no hydrogen atoms beta to the central arylene group or to the amino groups. This invention also relates to stable, rigid polymers derived from said diamines.

2. Description of the Art

Neopentyl diamine is known and polyamides have been made from this diamine. No aromatic bis(neopentylamine) has been found in the art.

U.S. Pat. No. 2,497,673 to Kirk Jr. (I) discloses diamines of the formula

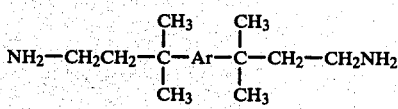

wherein Ar includes certain of the Ar groups described in the instant application.

U.S. Pat. No. 2,464,693 to Kirk Jr. (II) discloses diamines of the formula

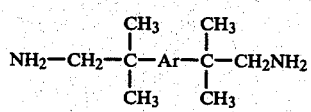

wherein Ar includes certain of the Ar groups described in the instant application.

U.S. Pat. No. 2,900,369 to Edwards et al discloses a diamine having the formula

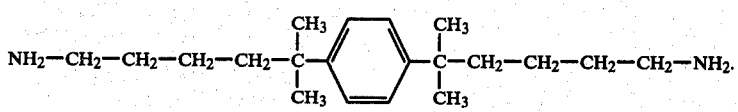

U.S. Pat. No. 3,422,143 to Bottomley discloses diamines of the formula

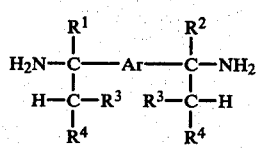

where $R^1$ and $R^2$ are lower alkyl, $R^3$ and $R^4$ are hydrogen or lower alkyl wherein Ar includes certain of the Ar groups described in the instant application.

The above-cited patents disclose homologs and an isomer of the diamines of this invention. These known diamines have the general formula

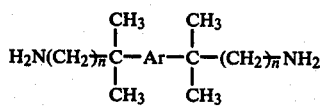

wherein n is 0, 1, 2 or 4. All of these diamines contain hydrogen atoms in positions beta to arylene or to nitrogen, or both. Such diamines provide polymers which are demonstrably inferior in thermal stability to polymers prepared from diamines of this invention which contain no hydrogen atoms beta to either arylene or nitrogen. In this regard see the Comparative Examples preceding the claims.

British Pat. No. 799,762 to Bataafsche discloses diamines of the formula

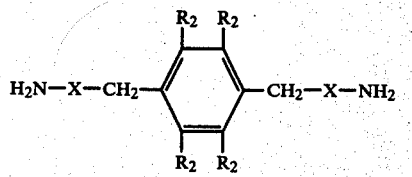

where $R_2$ represents the same or different alkyl groups of 1 to 6 carbon atoms, and X represents an alkylene group containing 2 to 5 carbon atoms. All of the "X" alkylene groups actually disclosed are straight chain alkylene groups containing only repeating —$CH_2$— groups; such diamines contain hydrogen atoms beta to both arylene and nitrogen. Finally, this patent contains no enabling disclosure for preparing the diamines of the instant invention.

U.S. Pat. No. 3,175,007 to Berhenke discloses various dianilines which are diamines of the formula

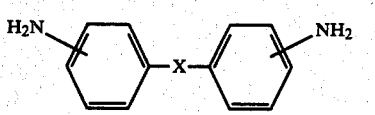

where —X— is —O—, —S—,

or a lower alkylidene radical. One disclosed compound, methylenedianiline (column 2, line 23), is without aliphatic beta hydrogen atoms but is completely different structurally from the diamines of the instant invention.

SUMMARY OF THE INVENTION

There have now been discovered aromatic-aliphatic diamines of the formula

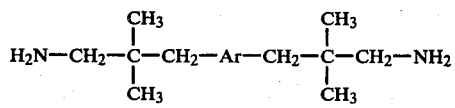

where Ar is an arylene selected from the group consisting of 1,2-phenylenes, 1,3-phenylenes, 1,4-phenylenes, 2,2'-biphenylenes, 3,3'-biphenylenes, 4,4'-biphenylenes, and 2,6-naphthylenes, said arylene being unsubstituted or substituted with methyl or chloro.

There have further been discovered thermally stable, rigid, polyamides, polyureas and polyurethanes having the repeating unit

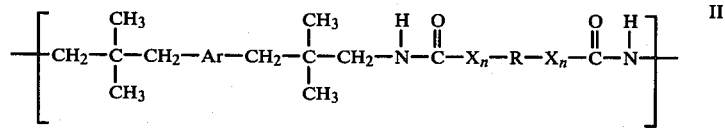

in which Ar is arylene as defined above, X is —NH— or —O—, n is 0 or 1, and R is Ar, alkylene of 1 to 20 carbon atoms or oxygen-interrupted alkylene of 3 to 20 chain atoms, particularly $+CH_2-CH_2-O)_{\overline{m}}CH_2-CH_2-$ where m is 1 to 6. The term "rigid" denotes the presence of a sufficient quantity of aromatic rings in the backbone of the polymer to provide stiffness.

When n is 0, formula II represents the repeating unit of a polyamide. When n is 1 and X is —NH—, formula II represents the repeating unit of a polyurea. When n is 1 and X is —O—, formula II represents the repeating unit of a polyurethane.

DESCRIPTION OF THE PREFERRED EMBODIMENTS

The novel diamines of formula I are prepared by heating a dinitrile of the formula

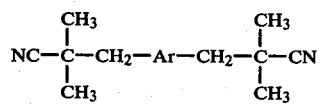

in which Ar is arylene as defined above with a dialkylaluminum hydride, preferably diisobutylaluminum hydride, for several hours in an inert anhydrous nonprotic solvent, e.g., a hydrocarbon and preferably an aromatic hydrocarbon, at a temperature sufficiently elevated above room temperature, e.g., 120° C., so that the reaction occurs at a convenient rate, under a dry inert atmosphere such as nitrogen, argon, helium and the like. After the reaction period is over, the intermediate aluminum salts are hydrolyzed by the gradual addition of a solution of water in a lower aliphatic alcohol, e.g., methanol. The following equations are believed to represent the steps involved.

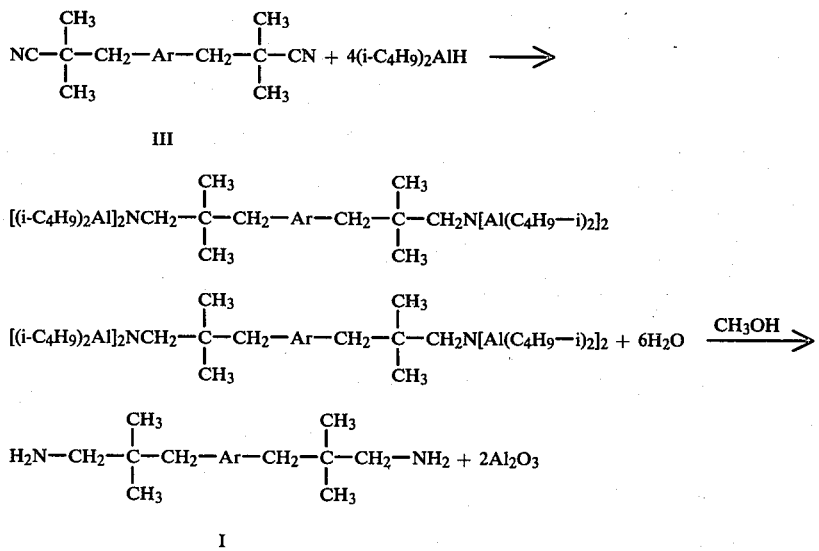

The by-product hydrated aluminum oxide is removed by filtration and the desired diamine is isolated and purified by conventional means.

The dinitriles of formula III are prepared by reacting the lithium salt of isobutyronitrile, generated in situ, with an α,α'-dihaloaromatic compound of the formula X—CH₂—Ar—CH₂—X      IV in which Ar is arylene as defined above, and X is Br or Cl at a temperature low enough to prevent the undesired decomposition of the lithium salt, e.g., in the range of −50° to −100° C., in a medium which at the appropriate temperature is a satisfactory solvent for both the lithium salt and the α,α'-dihaloaromatic compound, and under an inert dry atmosphere, e.g., nitrogen, helium, argon and the like, according to the following equation:

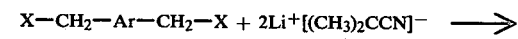

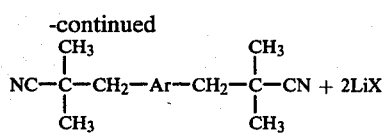

The solvent must also be nonreactive with the lithium salt, and its progenitors, e.g., it must be nonprotic. Ethers, especially cyclic ethers, e.g., tetrahydrofuran, are preferred solvents.

The lithium salt is generated in the reaction medium at the appropriate temperature by first reacting a hindered secondary amine, such as diisopropylamine, with a lower alkyllithium, such as n-butyllithium, to bring about the formation of the lithium salt of the hindered secondary amine, followed by addition of anhydrous isobutyronitrile. After allowing an appropriate time for the reaction to take place at the prescribed temperature, e.g., at least several hours, the reaction mixture is allowed to warm to room temperature, and the product is isolated and purified by conventional methods.

The arylene groups embraced in the definition of Ar above are readily obtained by selection of the $\alpha,\alpha'$-dihaloaromatic compound of formula IV. For example, suitable compounds include:

$\alpha,\alpha'$-dibromo-m-xylene
$\alpha,\alpha'$-dibromo-p-xylene
$\alpha,\alpha'$-dibromo-o-xylene
$\alpha,\alpha'$-dichloro-m-xylene
$\alpha,\alpha'$-dibromo-2-chloro-p-xylene
$\alpha,\alpha'$-dibromo-2-methyl-p-xylene
3,6-bis(chloromethyl)durene
2,2'-bis(bromomethyl)biphenyl
2,2'-bis(chloromethyl)biphenyl
3,3'-dichloro-4,4'-bis(bromomethyl)biphenyl
3-chloro-4,4'-bis(bromomethyl)biphenyl
2,6-bis(bromomethyl)naphthalene
2,6-bis(chloromethyl)naphthalene
1,5-dichloro-2,6-bis(bromomethyl)naphthalene
1-chloro-2,6-bis(bromomethyl)naphthalene
3,3'-bis(bromomethyl)biphenyl
4,4'-bis(bromomethyl)biphenyl
4,4'-bis(chloromethyl)biphenyl
and the like.

The polyamides are prepared by reacting the diamines with either acid chlorides of dibasic acids in the presence of an acid acceptor, or with diphenyl esters of dibasic acids. With the acid chlorides of aliphatic dibasic acids, e.g., sebacyl chloride, usually carried out at ambient temperature, but higher or lower temperatures are also satisfactory. The isolation of the product usually involves the addition of a nonsolvent for the polymer, followed by thorough washing of the polymer in water. These procedures are discussed by P. W. Morgan in "Condensation Polymers by Interfacial and Solution Methods", Wiley, 1965.

A convenient method for the preparation of polyamides from the acid chlorides of aromatic dibasic acids, e.g., terephthaloyl chloride, involves an interfacial polymerization technique in which the diamine is dispersed in a rapidly stirred mixture of water, an inert water-immiscible solvent, e.g., chloroform, carbon tetrachloride and the like, a dispersing agent, e.g., sodium lauryl sulfate, and a water soluble acid acceptor, e.g., sodium carbonate. The acid chloride, dissolved in the same inert, water-immiscible solvent, is then added rapidly. Such procedures and the methods for isolating and purifying the products are also described by P. W. Morgan in the reference noted above.

Suitable acid chlorides of dibasic acids for reacting with the diamines of this invention to prepare polyamides include:

adipyl dichloride
sebacyl dichloride
malonyl dichloride
phthaloyl dichloride
isophthaloyl dichloride
terephthaloyl dichloride
chloroterephthaloyl dichloride
methylterephthaloyl dichloride
ethylterephthaloyl dichloride
5-tert-butylisophthaloyl dichloride
tetrafluoroterephthaloyl dichloride
tetrachloroterephthaloyl dichloride
tetrabromoterephthaloyl dichloride
tetraiodoterephthaloyl dichloride
tetramethylterephthaloyl dichloride
2,5-diphenylterephthaloyl dichloride
4,4'-biphenyldicarbonyl dichloride
2,2',3,3',5,5',6,6'-octafluoro-4,4'-biphenyldicarbonyl dichloride
2,2'-dibromo-4,4'-biphenyldicarbonyl dichloride
2,2',6,6'-tetrachloro-4,4'-biphenyldicarbonyl dichloride
2,2'-diiodo-4,4'-biphenyldicarbonyl dichloride
2,2'-dimethyl-4,4'-biphenyldicarbonyl dichloride
4,4'-oxydibenzoyl dichloride
3,3'-dimethyl-4,4'-oxydibenzoyl dichloride
2,6-naphthalenedicarbonyl dichloride

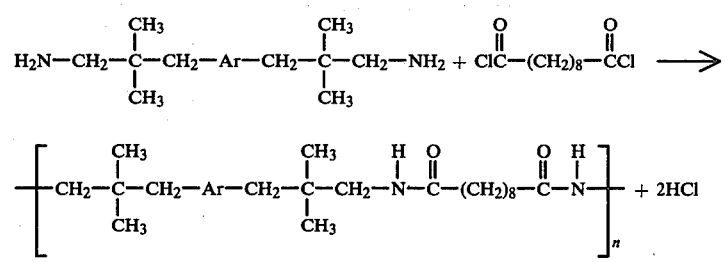

a convenient method for preparing the polyamides comprises a solution polymerization in which a solution of the acid chloride in an inert nonprotic solvent, e.g., chloroform, carbon tetrachloride, and the like, is added quickly to a stirred solution of the diamine and a tertiary amine, e.g., triethylamine, as the acid acceptor, in the same solvent. These condensation polymerizations are 1,3,4,5,7,8-hexachloro-2,6-naphthalenedicarbonyl dichloride
1,4-cyclohexanedicarbonyl dichloride
1-methyl-2,3-cyclobutanedicarbonyl dichloride
bis(4-chlorocarbonylphenyl)methane
bis(4-chlorocarbonylphenyl)dichloromethane 2,2-bis(4-chlorocarbonylphenyl)propane
and the like.

To prepare polyamides by reactions of the diamines with diphenyl esters, it is only necessary to intimately mix the diamine and the diphenyl ester in a suitable vessel and then apply heat so that an exchange reaction occurs with the expulsion of phenol:

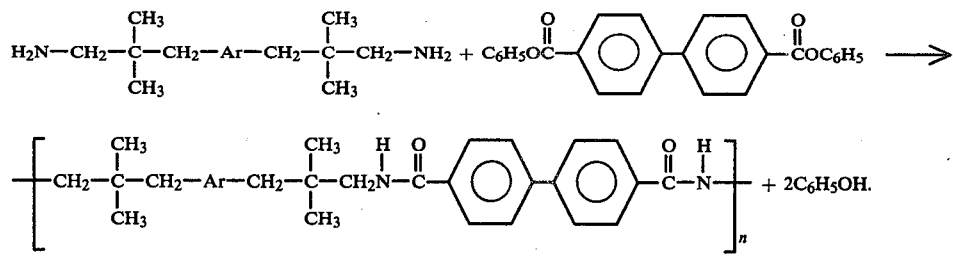

At temperatures of about 200° C. and higher the reaction occurs at a convenient rate, and is completed in a few hours. The temperature can be raised in the later portion of the reaction period to facilitate the driving off of by-product phenol. The removal of phenol is also facilitated by evacuation of the reaction vessel, e.g., with an oil pump. When the reaction is completed, the polymer is isolated and purified by conventional methods. Exchange reactions for the preparation of polyamides from diamines and the aryl esters of dibasic acids are described in "Encyclopedia of Polymer Science and Technology", Vol. 10, p. 487, Wiley, 1969. The diphenyl esters corresponding to the diacid chlorides listed above may be used in this exchange reaction with the diamines of this invention to prepare polyamides.

Polyureas are prepared by reacting diamines of formula I with diisocyanates using the general procedure of Example 15 below.

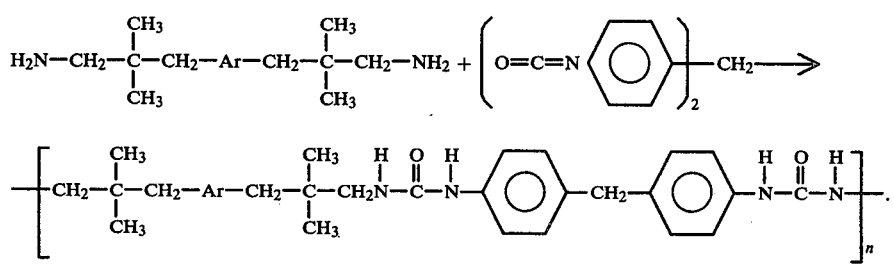

When other diisocyanates are substituted for the bis(4-isocyanatophenyl)methane in that procedure, the corresponding polyureas are obtained. Other polyureas are obtained by using other diamines of formula I.

Suitable diisocyanates for use in preparing the polyureas of this invention include:
tetramethylene diisocyanate
hexamethylene diisocyanate
1,3-phenylene diisocyanate
4-methyl-1,3-phenylene diisocyanate
1,4-phenylene diisocyanate
4,4'-biphenylene diisocyanate
3,3'-dimethyl-4,4'-biphenylene diisocyanate
bis(4-isocyanatophenyl)methane
2,2-bis(4-isocyanatophenyl)propane
bis(4-isocyanatophenyl)ether
1,4-cyclohexylene diisocyanate
and the like.

Polyurethanes are prepared by reacting diamines of formula I with bischloroformates using the general procedure of Example 16 below.

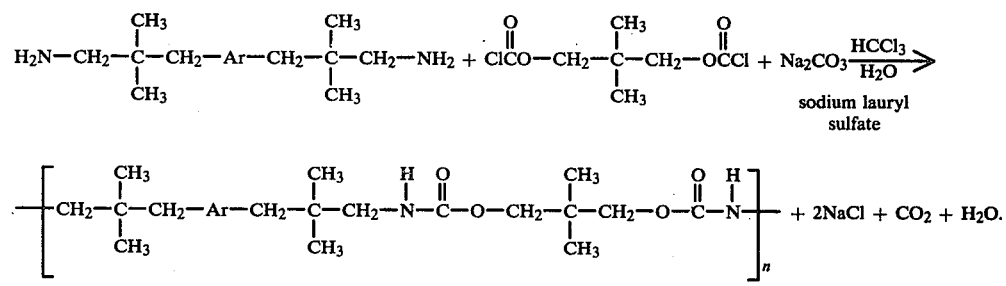

When other bischloroformates are substituted for the bischloroformate of neopentyl glycol in this procedure, the corresponding polyureas are obtained. Other polyurethanes are obtained by using other diamines of formula I.

Suitable bischloroformates for use in preparing the polyurethanes of this invention include:
ethylene bischloroformate
trimethylene bischloroformate
2,2-dimethyltrimethylene bischloroformate
1,4-cyclohexylene bischloroformate
p-phenylene bischloroformate
2,2-bis(4-chlorocarbonyloxyphenyl)propane 2,2-bis(4-chlorocarbonyloxy-3,5-dichlorophenyl)-propane
3-oxapentane-1,5-bischloroformate
and the like.

Because the diamines of this invention are free of hydrogen atoms beta to the amino groups, the polyamides, polyureas and polyurethanes prepared from these diamines are much superior in thermal stability to the corresponding polymers having beta hydrogen atoms. This is particularly advantageous in melt processing these polymers, for example, in melt spinning of fibers. The most thermally stable of these polymers, and therefore a preferred group, are the polymers of formula II in which R is Ar as defined above.

EXAMPLES OF THE INVENTION

The following examples illustrate the novel diamines, polyamides, polyureas and polyurethanes of this invention and their preparation. In these examples parts are by weight unless otherwise indicated, and all temperatures are expressed in degrees Centigrade. All equipment was dried in an oven at 135° before assembly and flushed with dry nitrogen after assembly. Weighing and handling of all the diamines was carried out in a nitrogen dry box. The alcohol used in these examples was 95% ethanol denatured with benzene.

EXAMPLE 1

(a) 1,4-Bis(2-methyl-2-cyanopropyl)benzene

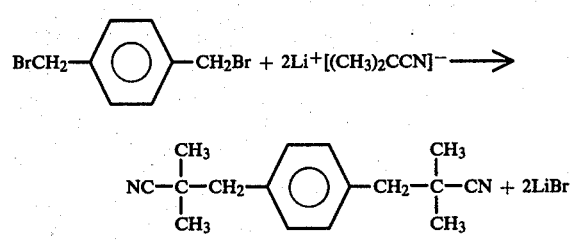

In a 2-liter flask, equipped with a magnetic stirrer, a reflux condenser capped with a nitrogen bubbler, a dropping funnel, and a syringe adapter, was placed 900 ml of anhydrous tetrahydrofuran (THF) and 42 ml (30.32 g, 0.30 M) of diisopropylamine (via syringe). The stirred mixture was cooled in a dry ice-acetone bath, and then 138.6 ml of 2.17 N (0.30 M) n-butyllithium in hexane was added via syringe. After the mixture had stirred for 1 hr., a solution of 20.52 g (0.297 M) of freshly distilled isobutyronitrile in 60 ml of anhydrous THF was added in 20 minutes. Following an additional 1 hr and 7 min of stirring at dry ice temperature, a solution of 39.57 g (0.150 M) of α,α'-dibromo-p-xylene in 450 ml of anhydrous THF was added in 1 hr 23 min. The mixture was stirred at dry ice temperature for 2 hr 15 min and then overnight as the cooling bath warmed to room temperature. Stirring was continued for 4 days at room temperature. The suspended white solid was removed by filtration, rinsed on the filter with THF and dried: WT=13.74 g, mp=193° to 195°. The filtrate was distilled on the water pump to remove the solvent, and the residue, a mixture of brown oil and solid, was stirred and 100 ml of methanol which dissolved the brown oil. Filtration of the mixture, rinsing of the solid on the filter with methanol, and drying of the solid under nitrogen gave an additional 15.7 g of crude 1,4-bis(2-methyl-2-cyanopropyl)benzene melting at 192° to 194.5°° (total yield=82%). Dissolving of this material in refluxing acetone (28.5 ml/g), filtration of the hot solution through a course sintered glass funnel to remove some insoluble material, and cooling of the filtrate at 8° to 10° gave the product as colorless needles melting at 194° to 195°.

Anal. Calc'd for $C_{16}H_{20}N_2$: C, 79.95; H, 8.39; N, 11.66. Found: C, 79.79; 79.96; H, 8.21; 8.37; N, 11.83; 11.67.

(b) 1,4-Bis(2,2-dimethyl-3-aminopropyl)benzene

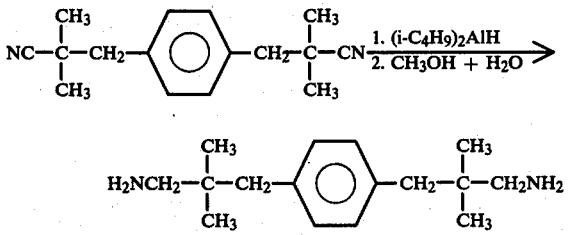

In a 2-liter flask, equipped with a magnetic stirrer, a reflux condenser capped with a nitrogen bubbler, and an addition funnel, was placed 7.50 g (0.0312 M) of 1,4-bis(2-methyl-2-cyanopropyl)benzene and 300 ml of reagent grade toluene which had been passed through acid alumina under nitrogen directly into the reaction vessel. With stirring at room temperature, 107 ml of a 24.1% solution (0.150 M) of diisobutylaluminum hydride in toluene was added from the addition funnel in 28 minutes. The mixture was then refluxed for 16 hrs. After the mixture had been cooled in an ice-water bath, a solution of 6 ml of water in 30 ml of methanol was added dropwise with stirring. This was followed by the dropwise addition of a solution of 30 ml of water in 60 ml of methanol. The mixture was stirred vigorously for 1 hr while being cooled in the ice-water bath, and then for an additional hour at room temperature. The mixture was filtered under nitrogen, the solid was washed thoroughly on the filter with toluene, and the combined filtrate and rinsings were distilled on the water pump. The resulting residue crystallized on cooling to room temperature. Further drying on the oil pump gave 5.28 g (68%) of crude 1,4-bis(2,2-dimethyl-3-aminopropyl)-benzene melting at 53° to 56° to a cloudy melt. Distillation of this material through a small Vigreux still gave the product as a colorless liquid boiling at 131° to 132°/0.60 mm. The solidified material melted to a clear melt at 53.5° to 54.75°.

Anal. Calc'd for $C_{16}H_{28}N_2$: C, 77.36; H, 11.36; N, 11.28. Found: C, 77.68; 77.07 77.15; H, 11.44; 11.30; 11.27; N, 11.04; 11.14.

The infrared spectrum contains bands at 2.93, 3.00 and 6.15μ (—$NH_2$), 3.28μ (shoulder) (=CH), 3.38 and 3.48μ (saturated CH), 6.59 and 6.77μ (aromatic C=C), 7.21 and 7.33μ (gem-dimethyl), and 11.86μ (p-disubstituted aromatic).

EXAMPLE 2

(a) 1,3-Bis(2-methyl-2-cyanopropyl(benzene)

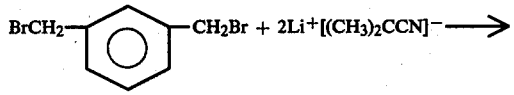

-continued

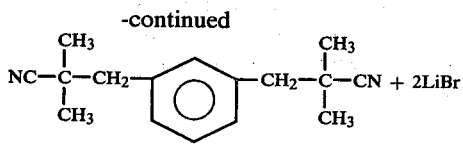

In a dry 2-liter flask, equipped with a large magnetic stirrer, a reflux condenser capped with a nitrogen bubbler, an addition funnel, and a syringe adapter, was placed 900 ml of anhydrous THF and 42 ml (30.32 g, 300 M) of diisopropylamine (via syringe). The mixture was cooled in a dry ice-acetone bath and, with stirring, 125.3 ml of 2.4 molar (0.300 M) n-butyllithium in hexane was added via syringe. After the mixture had stirred for 1 hr 35 min, 20.52 g (0.297 M) of freshly distilled isobutyronitrile in 60 ml of THF was added in 30 minutes. Following another 70 minutes of stirring, 39.57 g (0.150 M) of α,α'-dibromo-m-xylene was added all at once. The mixture was stirred for 2 hrs at −76°, and then overnight as the cooling bath warmed to room temperature. After an additional day of stirring at room temperature, the mixture was distilled on the water pump to yield a semisolid residue. Dissolving this material in 700 ml of chloroform, followed by three extractions of the resulting solution with 200 ml of water (with HCl acidification during the first extraction), drying over anhydrous magnesium sulfate, and removal of the solvent on the water pump, gave 35.5 g (98%) of a slowly crystallizing, brown solid. This material was further dried on an oil pump: mp=58° to 63°. All of this material was stirred with 2 liters of refluxing cyclohexane, but an appreciable quantity of an oily material was insoluble. Decanting of the solution from this oil, followed by cooling, yielded 18.0 g of 1,3-bis(2-methyl-2-cyanopropyl)benzene as almost colorless prisms melting at 69° to 70°. Refluxing of the filtrate with Darco, followed by filtration, evaporation to about 500 ml, seeding, and cooling, yielded an additional 0.16 g of product melting at 68° to 70°.

Anal. Calc'd for $C_{16}H_{20}N_2$: C, 79.95; H, 8.39; N, 11.66. Found: C, 79.88; 79.69; H, 8.04; 8.31; N, 11.74; 11.56.

(b) 1,3-Bis(2,2-dimethyl-3-aminopropyl)benzene

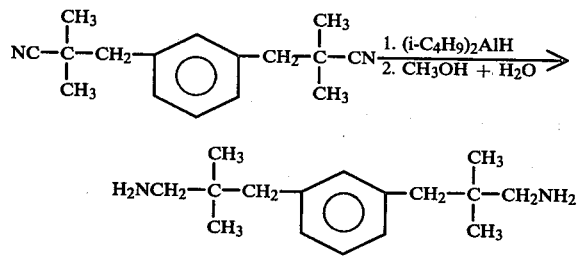

In a 1-liter flask equipped with a paddle stirrer, a reflux condenser capped with a nitrogen bubbler, and an addition funnel, was placed 7.50 g of 1,3-bis(2-methyl-2-cyanopropyl)benzene and 250 ml of reagent grade toluene which had been passed through acid alumina under nitrogen directly into the reaction vessel. With stirring at room temperature, 107 ml of a 25% solution of diisobutylaluminum hydride in toluene was added in 1 hr. The mixture was refluxed for 17 hrs 15 min. The mixture was then worked up as described in Example 1(b). Upon distillation of the isolated product through a small Vigreux still, there was otained 3.51 g of 1,3-bis(2,2-dimethyl-3-aminopropyl)benzene as a colorless liquid distilling at 105° to 110°/0.05 mm.

Anal. Calc'd for $C_{16}H_{28}N_2$: C, 77.36; H, 11.36; N, 11.28. Found: C, 77.59; 77.29; H, 11.31; 11.23; N, 11.36; 11.50.

EXAMPLE 3

(a) 1,4-Bis(2-methyl-2-cyanopropyl)tetramethylbenzene

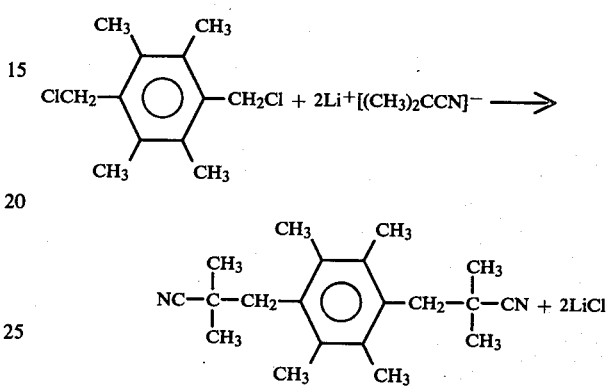

In a 1-liter flask, equipped with a magnetic stirrer, a reflux condenser capped with a nitrogen bubbler, an addition funnel, and a syringe adapter, was put 500 ml of anhydrous THF and 14 ml (10.10 g, 0.10 M) of diisopropylamine (via syringe). The flask was cooled in a dry ice-acetone bath and, with stirring, 41.8 ml of 2.4 molar (0.100 M) n-butyllithium in hexane was added via a syringe. The mixture was stirred for 1 hr, and then a solution of 6.48 g (0.094 M) of freshly distilled isobutyronitrile in 20 ml of anhydrous THF was added in 20 minutes. After an additional 65 minutes of stirring, 11.55 g (0.050 M) of 3,6-bis(chloromethyl)durene was added all at once. The mixture was stirred for 5 hrs at −76°, and then overnight as the cooling bath warmed to room temperature. Filtration of the solid, rinsing on the filter with THF, and drying under nitrogen, yielded 8.50 g of crude 1,4-bis(2-methyl-2-cyanopropyl)tetramethylbenzene melting at 187° to 190°. Evaporation of the filtrate to dryness yielded additional solid which was dissolved in 325 ml of chloroform. Extraction of this solution three times with 100 ml of water (with HCl-acidification during the first extraction), drying of the chloroform solution over anhydrous magnesium sulfate, and removal of the solvent in vacuo, yielded an additional 5.30 g of crude product (93% total yield) melting at 162° to 180°. Recrystallization of this material from acetone yielded the product as colorless needles melting at 192.5° to 193°.

Anal. Calc'd for $C_{20}H_{28}N_2$: C, 81.03; H, 9.52; N, 9.45. Found: C, 81.31; 81.14; H, 9.35; 9.57; N, 9.46; 9.41.

The infrared spectrum of this material contains bands at 3.31μ (≡CH), 3.35 and 3.40μ (saturated CH), 4.48μ (—C≡N), 6.69μ (aromatic C═C) and 7.18 and 7.30μ (gem-dimethyl).

(b) 1,4-Bis(2,2-dimethyl-3-aminopropyl)tetramethylbenzene

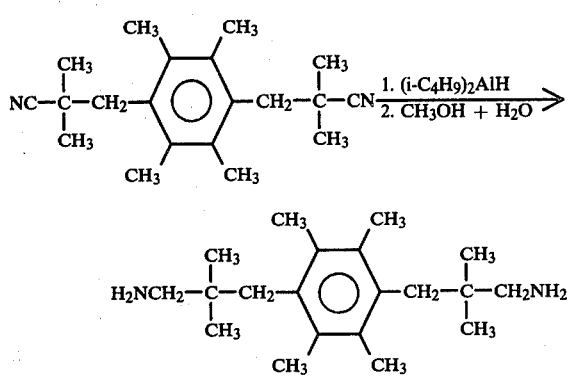

In a 1-liter flask, equipped as described in Example 1(b), was put 6.17 g of 1,4-bis(2-methyl-2-cyanopropyl)-tetramethylbenzene and 200 ml of reagent grade toluene which had been passed through acid alumina under nitrogen directly into the reaction vessel. With stirring at room temperature, 71.3 ml of a 24.1% solution of diisobutylaluminum hydride in toluene was added in 25 min. The mixture was refluxed for 22 hrs and allowed to stand at room temperature for 3 days. After the mixture had been cooled in an ice-water bath, a solution of 4 ml of water in 20 ml of methanol was added dropwise with stirring. This was followed by the dropwise addition of a solution of 20 ml of water in 40 ml of methanol. The mixture was then stirred at room temperature for several hours and allowed to stand at room temperature for 3 days. The mixture was filtered under nitrogen, the solid was washed thoroughly with toluene on the filter, and the combined filtrate and rinsings were distilled on the water pump. A solid residue resulted which, after further drying in a vacuum oven at room temperature, weighed 5.21 g and melted at 97° to 99°. Sublimation of this material at 125° to 145°/0.50 mm gave 1,4-bis(2,2-dimethyl-3-aminopropyl)tetramethylbenzene as a colorless crystalline solid melting at 97.5° to 98.5°.

Anal. Calc'd for $C_{20}H_{36}N_2$: C, 78.88; H, 11.92; N, 9.20. Found: C, 78.62; 78.55; H, 12.05; 12.08; N, 9.89; 10.09.

The infrared spectrum contains bands at 2.96, 3.03, and 6.20μ ($-NH_2$), 3.38 and 3.43μ (saturated CH), 6.73μ (aromatic C=C), and 7.23 and 7.36μ (gem-dimethyl).

EXAMPLE 4

(a) 3,3′-Bis(2-methyl-2-cyanopropyl)biphenyl

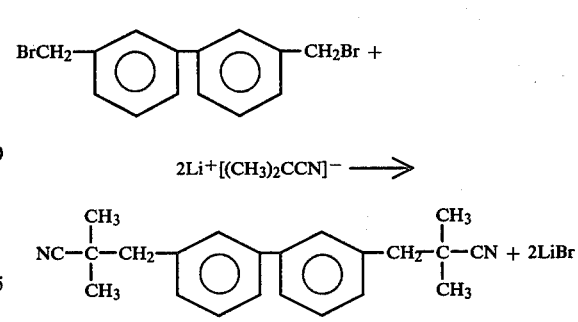

In a 500-ml flask, equipped with a magnetic stirrer, a reflux condenser capped with a nitrogen bubbler, a dropping funnel and a syringe adapter, was put 150 ml of anhydrous THF and 7.0 ml (5.05 g, 0.050 M) of diisopropylamine (via syringe). The flask was cooled in a dry ice bath, and with stirring, 23.1 ml of 2.17 molar (0.050 M) n-butyllithium in hexane was added via syringe. The mixture was stirred for 55 minutes, and then a solution of 3.42 g (0.049 M) of freshly distilled isobutyronitrile in 10 ml of anhydrous THF was added dropwise in 7 minutes. After an additional 20 minutes of stirring, a solution of 8.50 g (0.0250 M) of 3,3′-bis(bromomethyl)-biphenyl in 75 ml of anhydrous THF was added during 38 minutes. The mixture was allowed to warm to room temperature as it stirred overnight. During the addition, the mixture developed an intense blue color. This color was still apparent on the day after the mixture had warmed to room temperature, but after two additional days of stirring at room temperature, the mixture was light brown and clear. The solvent was removed on the water pump and the resulting residue was dissolved in 200 ml of chloroform. Washing of this solution three times with 100 ml of water (whth HCl acidification during the first washing), drying the solution over anhydrous magnesium sulfate, removal of the solvent on the water pump, and drying the resulting residue in vacuo, gave 7.50 g (95%) of crude 3,3′-bis(2-methyl-2-cyanopropyl)biphenyl melting at 96° to 103°. Dissolving this material in hot cyclohexane, refluxing the resulting solution with Darco, filtering through Celite, evaporating the filtrate to 125 ml, and cooling it at 8° to 10°, gave 5.36 g of the product as colorless prisms melting at 106.5° to 108.5°.

Anal. Calc'd for $C_{22}H_{24}N_2$: C, 83.50; H, 7.64; N, 8.86. Found: C, 83.74; 83.57; H, 7.60; 7.53; N, 8.63; 8.60.

The infrared spectrum (KBr) contains bands at 3.25μ (=CH), 3.32, 3.37 and 3.44μ (saturated CH), 4.45 (—C≡N), 6.19 and 6.28μ (aromatic C=C) and 12.7 and 14.04μ (meta disubstitued benzene).

(b) 3,3′-Bis(2,2-dimethyl-3-aminopropyl)biphenyl

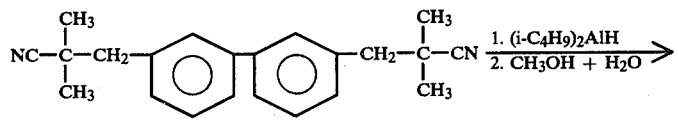

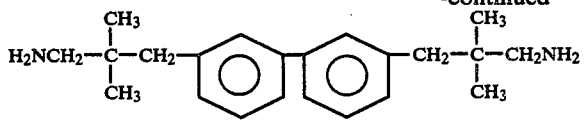

In a 2-liter flask, equipped as described in Example 1(b), was put 10.90 g of 3,3'-bis(2-methyl-2-cyanopropyl)biphenyl and 500 ml of reagent grade toluene which had been passed through acid alumina under nitrogen directly into the reaction vessel. With stirring at room temperature, 118 ml of a 25% solution of diisobutylaluminum hydride in toluene was added in 25 minutes. The mixture was refluxed for 18 hrs, and then allowed to stand at room temperature for 1 day. After the mixture had been cooled in an ice-water bath, a solution of 7 ml of water in 35 ml of methanol was added dropwise with stirring. This was followed by the dropwise addition of a solution of 33 ml of water in 66 ml of methanol. The ice-water bath was removed, and the mixture was stirred for 1 hour. The mixture was filtered under nitrogen, the solid was washed thoroughly with toluene on the filter, and the combined filtrate and rinsings were distilled on the water pump. The cloudy viscous residue weighed 10.8 g after it was evacuated for several hours with the oil pump at room temperature. Distillation of this material through a small Vigreux still gave 5.94 g of 3,3'-bis(2,2-dimethyl-3-aminopropyl)biphenyl as a clear, colorless, viscous liquid boiling at 159° to 168°/0.2–0.5 mm.

Anal. Calc'd for $C_{22}H_{32}N_2$: C, 81.42; H, 9.94; N, 8.63. Found: C, 81.31; 81.40; H, 10.19; 10.57; N, 8.29; 8.47.

EXAMPLE 5

(a) 2,6-Bis(2-methyl-2-cyanopropyl)naphthalene

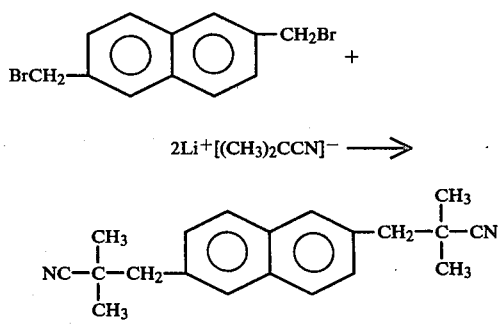

In a 1-liter flask, equipped as described in Example 4(a), was put 400 ml of anhydrous THF and 14.00 ml (10.10 g, 0.10 M) of diisopropylamine. The flask was cooled in a dry ice bath and, with stirring, 48.3 ml of 2.29 molar (0.111 M) n-butyllithium in hexane was added via a syringe. The mixture was stirred for 75 minutes and then 6.84 g of freshly distilled isobutyronitrile in 20 ml of anhydrous THF was added during 12 minutes. After an additional 23 minutes of stirring, 15.2 g of 2,6-bis(bromomethyl)naphthalene was added all at once. The mixture was stirred at −76° for 2½ hrs and then overnight as the bath warmed to room temperature. After an additional 3½ days of stirring at room temperature, the mixture was filtered and the resulting solid was rinsed on the funnel with THF and dried under nitrogen: wt=3.13 g, mp=181.8° to 184°. Evaporation of the filtrate to dryness on the water pump yielded additional solid which was dissolved in 700 ml of chloroform. Extraction of the chloroform solution three times with 300 ml of water (with HCl acidification during the first extraction), and removal of the solvent in vacuo yielded additional crude product, which after drying in a vacuum oven at room temperature, weighed 10.00 g and melted at 178° to 180°. Recrystallization of this material from acetone yielded 2,6-bis(2-methyl-2-cyanopropyl)naphthalene melting at 183.5° to 184.5°.

Anal. Calc'd for $C_{20}H_{22}N_2$: C, 82.71; H, 7.64; N, 9.65. Found: C, 83.21; 82.93; H, 7.84; 7.73; N, 9.70; 9.62.

The infrared spectrum of this material contains a C≡N stretch band at 4.45μ.

(b) 2,6-Bis(2,2-dimethyl-3-aminopropyl)naphthalene

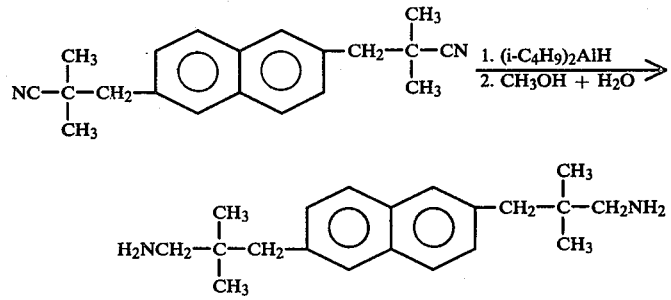

In a 1-liter flask, equipped as described in Example 2(b), was put 9.06 g of 2,6-bis(2-methyl-2-cyanopropyl)naphthalene and 300 ml of reagent grade toluene which had been passed through acid alumina under nitrogen directly into the reaction vessel. With stirring at room temperature, 107 ml of a 25% solution of diisobutylaluminum hydride in toluene was added in 55 minutes. The mixture was then refluxed for 20 hrs. After the mixture had been cooled in an ice-water bath, a solution of 6 ml of water in 30 ml of methanol was added with stirring during 55 minutes. This was followed by the addition of a solution of 30 ml of water in 60 ml of methanol during 1 hr 35 min. The mixture was stirred for 1 hr while being cooled in the ice-water bath and then at room temperature overnight. The mixture was filtered under nitrogen, the solid was washed thoroughly with toluene on the filter, and the combined filtrate and rinsings were distilled on the water pump.

The resulting solid residue, after being dried in vacuo for about 2 hrs, weighed 8.0 g and melted at 97° to 98.25°. Sublimation of this material at 145° to 165°/0.6 mm gave 2,6-bis(2,2-dimethyl-3-aminopropyl)naphthalene as a colorless, crystalline solid melting at 96.75° to 98.50°.

Anal. Calc'd for $C_{20}H_{30}N_2$: C, 80.48; H, 10.13; N, 9.39. Found: C, 82.09; 81.74; H, 10.45; 10.48; N, 9.85; 9.77.

The infrared spectrum contains bands at 2.98 and 3.06$\mu$ ($-NH_2$), 3.29$\mu$ (unsaturated CH), 3.38, 3.43 and 3.50$\mu$ (saturated CH), 6.23, 6.65 and 6.80$\mu$ ($-NH_2$ and/or aromatic C=C), and 7.22 and 7.33$\mu$ (gem-dimethyl).

EXAMPLE 6

(a) 4,4'-Bis(2-methyl-2-cyanopropyl)biphenyl

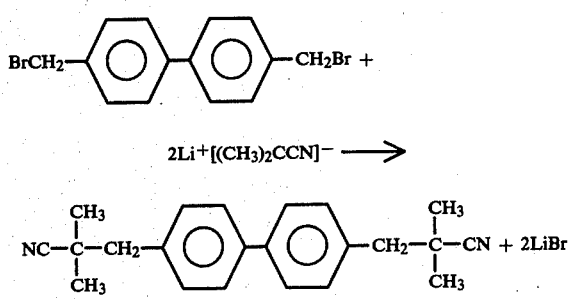

In a 500-ml flask, equipped as described in Example 4(a), was placed 250 ml of anhydrous THF and 7.00 ml of diisopropylamine (via syringe). The flask was cooled in a dry ice bath and, with stirring, 21.0 ml of 2.4 molar n-butyllithium in hexane was added via a syringe. The mixture was stirred for 1 hour and then 3.42 g of freshly distilled isobutyronitrile in 20 ml of THF was added in 20 minutes. After an additional hour of stirring, 8.50 g of 4,4'-bis(bromomethyl)biphenyl was added all at once. Stirring at $-76°$ was continued for several hours and overnight as the cooling bath warmed to room temperature. After an additional day of stirring, the solvent was distilled on the water pump. The resulting semisolid residue was dissolved in 500 ml of chloroform and the chloroform solution was extracted 4 times with water (with HCl acidification during the first extraction). Drying the solution over anhydrous magnesium sulfate, filtering, and removal of the solvent in vacuo gave 6.8 g of crude 4,4'-bis(2-methyl-2-cyanopropyl)biphenyl melting at 174° to 182°. After several recrystallizations from acetone, the product melted at 189.3° to 190.8°.

Anal. Calc'd for $C_{22}H_{24}N_2$: C, 83.50; H, 7.64; N, 8.86. Found: C, 82.81; 83.43; H, 7.94; 7.86; 7.90; N, 8.69; 8.79; 8.80.

(b) 4,4'-Bis(2,2-dimethyl-3-aminopropyl)biphenyl

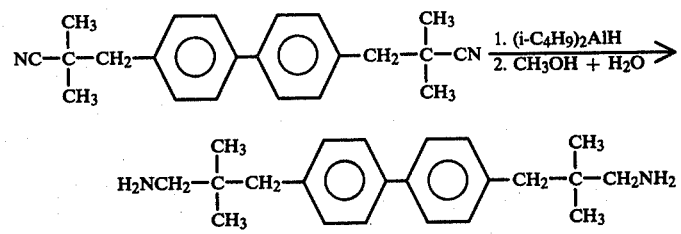

In a 1-liter flask, equipped as described in Example 2(b), was put 6.54 g of 4,4'-bis(2-methyl-2-cyanopropyl)biphenyl and 400 ml of reagent grade toluene which had been passed through acid alumina under nitrogen directly into the reaction vessel. With stirring at room temperature, 71 ml of a 25% solution of diisobutylaluminum hydride in toluene was added in 30 minutes. The mixture was then refluxed for 17 hrs 40 min. After the mixture had been cooled in an ice-water bath, a solution of 5 ml of water in 22 ml of methanol was added dropwise with stirring in 1 hr. This was followed by the dropwise addition of a solution of 20 ml of water in 40 ml of methanol in 1 hr. The mixture was stirred for 1 hr while being cooled in the ice bath and for 1 hr at room temperature. It then stood at room temperature for one day. The mixture was filtered under nitrogen, the solid was washed thoroughly with toluene on the filter, and the combined filtrate and rinsings were distilled on the water pump. The resulting solid, after drying in vacuo, weighed 5.5 g and melted at 97° to 99°. Sublimation at 185° to 200°/0.10 mm gave 4,4'-bis(2,2-dimethyl-3-aminopropyl)biphenyl as a colorless crystalline solid.

Anal. Calc'd $C_{22}H_{32}N_2$: C, 81.42; H, 9.94; N, 8.63. Found: C, 81.31; 81.29; H, 10.11; 10.36; N, 8.87; 8.68.

EXAMPLE 7

(a) 3,3'-Dichloro-4,4'-bis(2-methyl-2-cyanopropyl)biphenyl

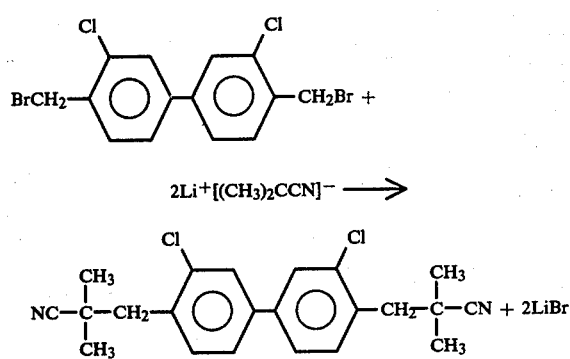

In a 500-ml flask, equipped as described in Example 4(a), was placed 150 ml of anhydrous THF and 7.0 ml of diisopropylamine (via syringe). The flask was cooled at $-76°$ and, with stirring, 21.0 ml of 2.4 molar n-butyllithium in hexane was added via syringe. The mixture was stirred for 1 hr 25 min and then 3.42 g of freshly distilled isobutyronitrile in 10 ml of THF was added in 20 minutes. After an additional 25 minutes of stirring, a solution of 10.22 g of 3,3'-dichloro-4,4'-bis(bromomethyl)biphenyl in 100 ml of THF was added with stirring during 1 hr 20 min. The mixture was stirred at $-76°$ for 1 hr 45 min and then overnight as the cooling bath warmed to room temperature. After an additional 2 days of stirring at room temperature, the solvent was removed in vacuo. The resulting residue was dissolved in 200 ml of chloroform and the chloroform solution was extracted 3 times with 100 ml of water (with HCl acidification during the first extraction). Drying the solution over anhydrous magnesium sulfate, filtering, and removal of the solvent in vacuo, gave 7.5 g of crude 3,3′-dichloro-4,4′-bis(2-methyl-2-cyanopropyl)biphenyl melting at 148° to 156°. A recrystallization from acetone, with a filtration of the hot solution to remove some insoluble material, gave product melting at 162° to 164°.

Anal. Calc'd for $C_{22}H_{22}Cl_2N_2$: C, 68.57; H, 5.76; Cl, 18.40; N, 7.27 Found: C, 68.36; 68.80; 68.28; H, 5.93; 6.09; 5.69; Cl, 18.14; 18.34; N, 7.48; 7.19.

(b)
3,3′-Dichloro-4,4′-bis(2,2-dimethyl-3-aminopropyl)-biphenyl

When an equivalent amount of 3,3′-dichloro-4,4′-bis(2-methyl-2-cyanopropyl)biphenyl is substituted for the 4,4′-bis(2-methyl-2-cyanopropyl)biphenyl in the procedure for Example 6(b), 3,3′-dichloro-4,4′-bis(2,2-dimethyl-3-aminopropyl)biphenyl of the formula

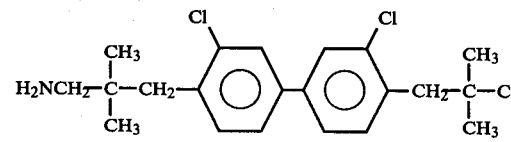

is formed.

EXAMPLE 8

A Polyamide from 1,4-Bis(2,2-dimethyl-3-aminopropyl)-benzene and Sebacyl Chloride

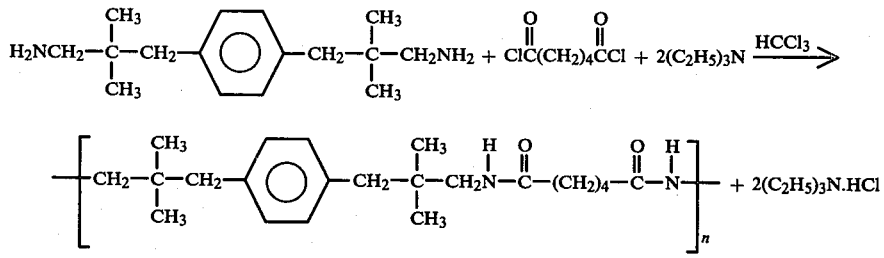

In a 3-liter flask, equipped with a paddle stirrer, a reflux condenser, and a nitrogen bubbler, was placed 25.00 g of 1,4-bis(2,2-dimethyl-3-aminopropyl)benzene, 31.0 ml of triethylamine, and 350 ml of chloroform which had been passed through basic alumina under nitrogen directly into the reaction flask. With vigorous stirring at room temperature, 24.07 g of freshly distilled sebacyl chloride in 100 ml of purified chloroform was added all at once. The mixture was stirred for 45 minutes and then 1500 ml of hexane was added to precipitate the polymer. After 15 minutes of stirring, the mixture was allowed to stand overnight. With stirring, a solution of 150 ml of concentrated hydrochloric acid in 600 ml of water was added. The coagulated polymer was filtered, rinsed on the filter with water, and then washed in a blender once with 600 ml of water, once with 600 ml of acetone and three times with 600 ml of water. The isolated polymer was dried overnight in a vacuum oven at 70°. There was thus obtained 32.6 g (78%) of product: inherent viscosity (0.05% in m-cresol at 25°)=1.32.

A clear, tough, colorless film was pressed from a portion of the polymer at 180° and 500 lbs pressure. Another portion of the polymer was melt spun through a spinnerette (0.020″×0.04″) at 248° to 270° to give filament which, after cold drawing, had strengths of about 1.5 grams/denier.

The product of another experiment, on 1/10 the scale of that just described, was further characterized by elemental analysis and infrared spectroscopy.

Anal. Calc'd for $(C_{26}H_{42}N_2O_2)_n$: C, 75.31; H, 10.21; N, 6.76. Found: C, 75.20; 75.66; H, 10.90; 10.89; N, 6.94; 6.95.

The infrared spectrum contained bands at $3.03\mu$ (—NH), 3.42 and $3.48\mu$ (saturated CH), 6.08 and $6.45\mu$ (amide I and II bands), $6.60\mu$ (aromatic C=C), and 7.30 and $7.32\mu$ (gem-dimethyl).

EXAMPLE 9

A Polyamide from 1,4-Bis(2,2-dimethyl-3-aminopropyl)-benzene and Adipyl Chloride

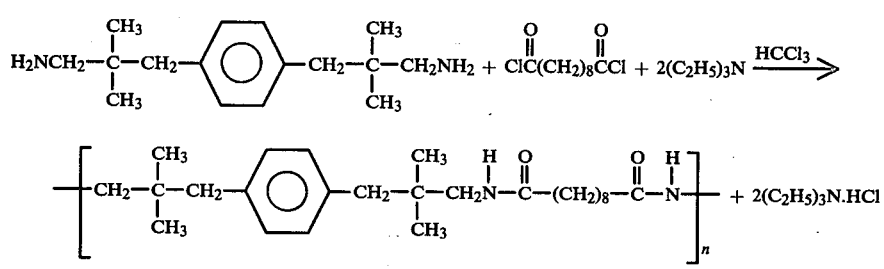

In a 300-ml flask, equipped as described in Example 8, was put 4.00 g of 1,4-bis(2,2-dimethyl-3-aminopropyl)-benzene, 5.0 ml of triethylamine, and 50 ml of chloroform which had been passed through basic alumina. With vigorous stirring at room temperature, a solution of 2.95 g of freshly distilled adipyl chloride in 20 ml of dried chloroform was added all at once. After a few minutes of stirring 25 ml of chloroform was added, and the mixture was stirred vigorously for ½ hr. Addition with stirring of 300 ml of hexane and 150 ml of alcohol gave a mushy precipitate which after filtration and stirring with water became a hard colorless solid. Evaporation of the filtrate and the rinsings to remove the hexane, gave more precipitate. The combined solids were dried in a vacuum oven at 70°, washed twice in a blender with 200 ml of water and then washed twice with 200 ml of methanol. The resulting polymer, after being dried in a vacuum oven at room temperature, weighed 2.00 g: inherent viscosity (0.05% in m-cresol at 25°)=0.73.

water. After being dried in a vacuum oven at 60°, it weighed 5.45 g (72%): inherent viscosity (0.05% in m-cresol, at 25°)=0.77. Long fibers could be drawn from a sample of the polymer heated on a metal block at 270° to 280°.

The infrared spectrum contained bands at 3.04μ (—NH), 3.39 and 3.43μ (saturated CH), 6.08 and 6.53μ (amide I and II bands), 6.69μ (aromatic C═C), and 7.32 and 7.34μ (gem-dimethyl).

EXAMPLE 11

A Polyamide from 1,4-Bis(2,2-dimethyl-3-aminopropyl)-benzene and Diphenyl Terephthalate

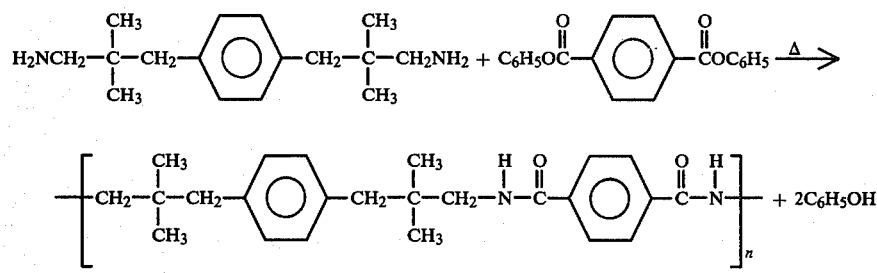

Anal. Calc'd for $(C_{22}H_{34}N_2O_2)_n$: C, 73.70; H, 9.56; N, 7.82. Found: C, 72.92; 73.07; H, 9.57; 9.63; N, 7.42; 7.50. Fibers could be hand drawn from the polymer heated on a metal block at 165° to 210°.

EXAMPLE 10

A Polyamide from 1,4-Bis(2,2-dimethyl-3-aminopropyl)-benzene and Terephthaloyl Chloride

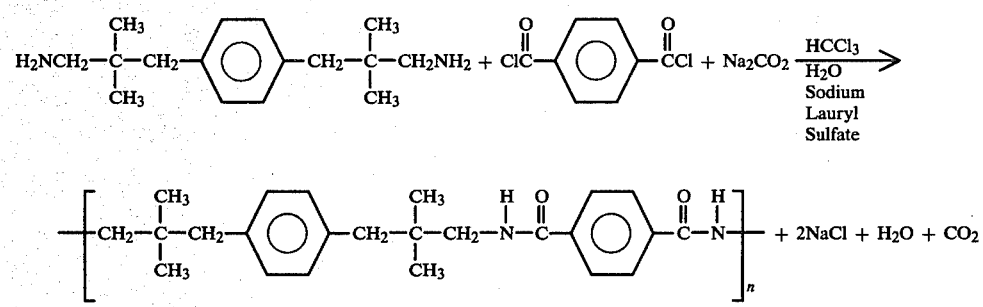

In a 1-liter blender was put 125 ml of distilled water, 50 ml of chloroform (which had been passed through basic alumina), 1.00 g of sodium lauryl sulfate, and 4.26 g of anhydrous sodium carbonate. The mixture was stirred moderately fast until a uniform emulsion was obtained. Then, 5.00 g of 1,4-bis(2,2-dimethyl-3-aminopropyl)benzene was added and stirring was continued for several minutes. A solution of 4.09 g of terephthaloyl chloride in 75 ml of purified chloroform was added with stirring in 30 seconds. After 5 minutes of vigorous stirring, 275 ml of hexane was added followed by 200 ml of alcohol. After a few additional minutes of stirring, the precipitated polymer was filtered, washed on the filter with water and alcohol and air dried. The isolated polymer was then washed twice in the blender with In a polymer tube (23 cm×2.5 cm), fitted with a side arm, was put 5.00 g of 1,4-bis(2,2-dimethyl-3-aminopropyl)benzene and 6.41 g of diphenyl terephthalate. A nitrogen capillary was positioned in the tube so that the end of the capillary was above the reaction mixture. The tube was lowered into the vapor of a 220° vapor bath and heated at that temperature for 3 hr 40 min. After 2 hrs and 20 min, solid polymer was evident. The tube was then heated in a 280° vapor bath for 2 hr 55 min. During the last 1 hr 45 min of this heating, the tube was evacuated at <0.5 mm. After the tube had cooled to room temperature, it was broken and 7.20 g (95%) of polymer was isolated. Successive washings of the polymer in a blender with 100 ml of water, 100 ml of acetone, and three times with 100 ml of water, and drying in a vacuum oven at 70° gave 6.61 g of product: inherent viscosity (0.05% in m-cresol at 25°)=0.49. A thermal gravimetric determination on this material shows that it does not begin to decompose until about 425°.

EXAMPLE 12

A Polyamide from
1,4-Bis(2,2-dimethyl-3-aminopropyl)-benzene and
Diphenyl Isophthalate

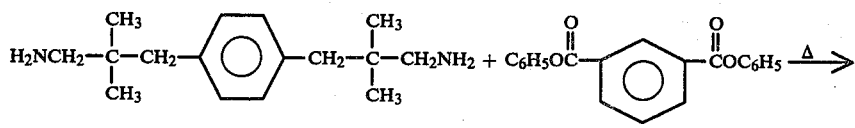

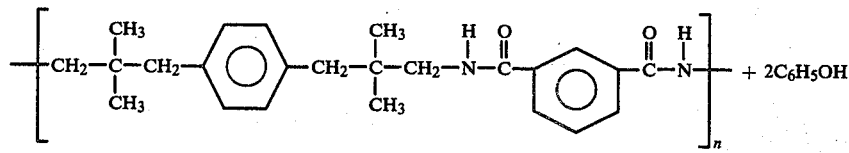

EXAMPLE 13

A Polyamide from
1,4-Bis(2,2-dimethyl-3-aminopropyl)benzene-and
Diphenyl Bibenzoate

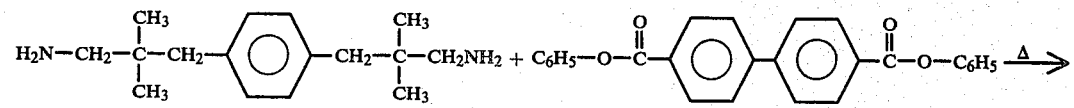

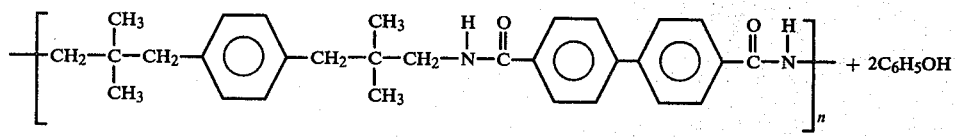

In a 50-ml flask was placed 5.00 g of 1,3-bis-(2,2-dimethyl-3-aminopropyl)benzene and 6.41 g of diphenyl iosphthalate. The flask was fitted with a 15-cm extension tube and a short path still head which had a nitrogen capillary inserted into it reaching to above the reaction mixture and a small round-bottomed flask as receiver. The assembled set-up was connected to a nitrogen bubbler. The flask was then heated in an oil bath at 220°. Within the first few minutes of heating, the charge became liquid, whereupon the flask was agitated to insure completed mixing of the reactants. The mixture became progressively more viscous as the heating was continued. After 3 hr 20 min of heating at 220°, the temperature of the oil bath was increased so that after 15 min the temperature was 268° to 270°. The oil bath was maintained at this temperature for 3 hr 5 min, during the final 1 hr 30 min of which the system was evacuated at about 0.5 mm. The reactor was then allowed to cool under vacuum. The polymer was isolated, ground up in a blender with 300 ml of water, reisolated by filtration, and finally dried in a vacuum oven at 70°: wt=7.0 gms. The inherent viscosity (0.05% in m-cresol at 25°)=0.32.

In a 50-ml round-bottomed flask was placed 5.00 g of 1,4-bis(2,2-dimethyl-3-aminopropyl)benzene and 7.94 g of diphenyl bibenzoate. The flask was then fitted with a 15-cm extension tube which had an adaptor for connecting to a nitrogen bubbler and for the insertion of a nitrogen capillary into the reaction vessel. The flask was then heated in an oil bath at 220° with the nitrogen capillary above the reaction mixture. Within the first few minutes of heating, the charge became liquid whereupon the flask was agitated to insure thorough mixing of the reactants. After 8 minutes of heating at 220°, the reaction mixture had resolidified. After 1 hr 8 min of heating at 220°, the temperature of the oil bath was increased so that at the end of an additional 2 hrs, the temperature was 265°. The reactor was then evacuated with an oil pump for 1 hr 35 min with the temperature maintained at 265° to 270°. The reactor was allowed to cool under vacuum. The isolated polymer was washed in a blender successively with 200 ml of water, 100 ml of acetone and then three times with 200 ml of water. After being dried in a vacuum overn at 70°, the polymer weighed 8.5 g: inherent viscosity (0.05% in m-cresol at 25°)=0.24.

EXAMPLE 14

A Polyamide from
1,4-Bis(2,2-dimethyl-3-aminopropyl)-benzene and
Diphenyl 2,6-Naphthalenedicarboxylate

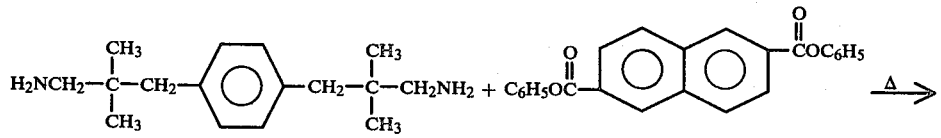

-continued

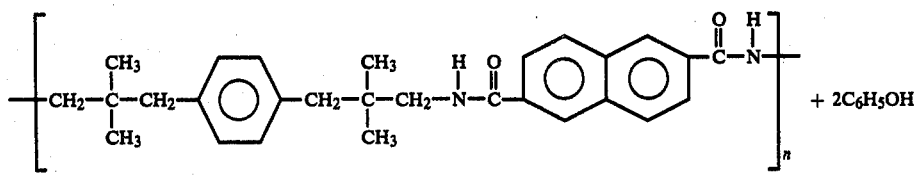

In a polymer tube (23 cm×2.5 cm) fitted with a side arm was put 5.00 g of 1,4-bis(2,2-dimethyl-3-aminopropyl)benzene and 7.41 g of diphenyl 2,6-naphthalenedicarboxylate. A nitrogen capillary was positioned in the tube so that the end of the capillary was above the reaction mixture. The tube was lowered into the vapor of a 220° vapor bath and heated at that temperature for 3 hrs 30 min. The tube was then heated in a 280° vapor bath for 2 hrs 45 min. During the last 1 hr 30 min of this heating, the tube was evacuated at 0.5 mm. After the tube had cooled to room temperature, it was broken and 8.00 g (93%) of polymer was isolated. After washing and drying as described in Example 11, there was obtained 7.60 g of product: inherent viscosity (0.05% in m-cresol at 25°)=0.45. A thermal gravimetric determination on this material shows that it does not begin to decompose until about 425°. A clear, brittle film was pressed at 320° and 500 lbs pressure.

EXAMPLE 15

A Polyurea from 1,4-Bis(2,2-dimethyl-3-aminopropyl)-benzene and Bis(4-isocyanatophenyl)methane polymer, isolated by filtration, was washed once in a blender with 300 ml of a 1:1 (by volume) solution of acetone and water, and then three times with 300 ml of water. After being dried in a vacuum oven at 70°, the polymer weighed 8.00 g (95%).

Anal. Calc'd for $(C_{31}H_{38}N_4O_2)_n$: C, 74.67; H, 7.68; N, 11.24. Found: C, 73.01; 72.73; H. 7.76; 7.57; N, 11.01; 10.98.

A colorless, transparent film was pressed from this polymer at 230° and 500 lbs pressure. Fibers could be drawn from the polymer on a metal block at 275° to 285°.

EXAMPLE 16

A Polyurethane from 1,4-Bis(2,2-dimethyl-3-aminopropyl)-benzene and the Bis-chloroformate of Neopentyl Glycol

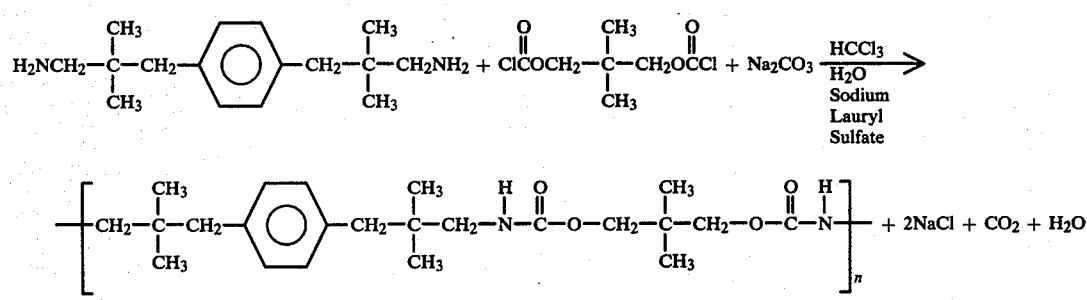

In a blender was put 150 ml of distilled water, 60 ml of chloroform (which had been passed through basic alumina), 1.20 g of sodium lauryl sulfate, 6.36 g of anhydrous sodium carbonate and 7.45 g of 1,4-bis(2,2-dimethyl-3-aminopropyl)benzene. The mixture was stirred until a uniform emulsion was obtained. Then a

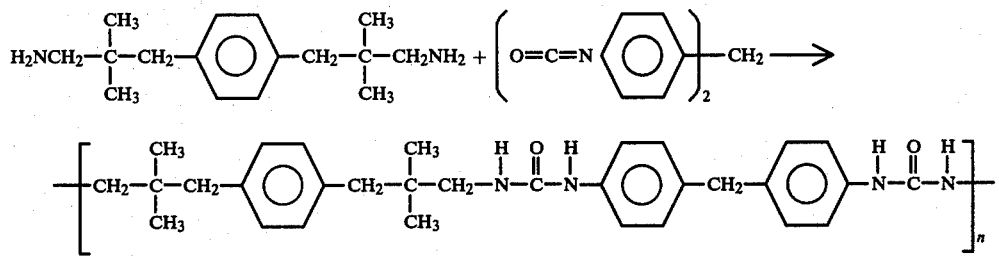

In a blender was put 4.225 g of bis(4-isocyanatophenyl)methane dissolved in 90 ml of a 70:30 mixture (by volume) of tetramethylene sulfone and chloroform. With vigorous stirring, a solution of 4.194 g of 1,4-bis(2,2-dimethyl-3-aminopropyl)benzene in 90 ml of the same solvent was added all at once. Vigorous stirring was continued for 10 minutes whereupon 130 ml of a 4% (by volume) solution of n-butylamine in water was added. This was followed by the addition of 350 ml of water and several additional minutes of stirring. The solution of 6.87 g of the bischloroformate of neopentyl glycol in 50 ml of purified chloroform was added in about 20 seconds with stirring. After 5 minutes of stirring, 500 ml of hexane was added. Stirring was continued for another 5 minutes. The polymer was isolated by filtration and washed in the blender twice with 200 ml of water, once with 200 ml of 1:1 (by volume) acetone: water, and once again with 200 ml of water. After being dried for several hours in a vacuum oven at 70°, the polymer weighed 8.3 g (68%): inherent viscosity (0.05%, in m-cresol at 25°)=0.67. A clear, colorless, tough film was pressed at 180° and 500 lbs pressure.

EXAMPLE 17

EXAMPLE 18

A Polyamide from 1,3-Bis(2,2-dimethyl-3-aminopropyl)-benzene and Diphenyl Bibenzoate

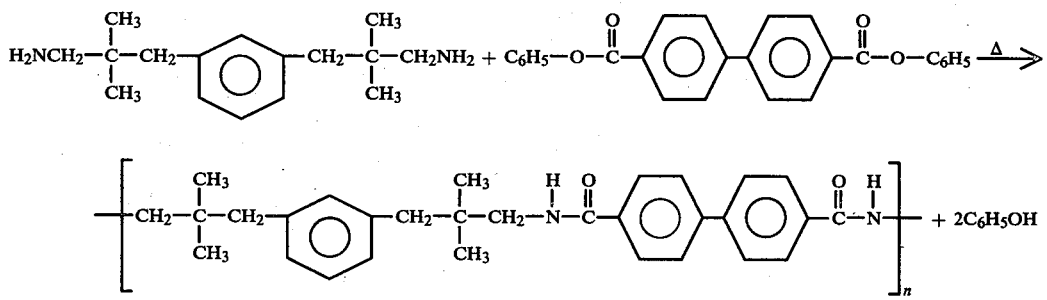

A Polyamide from 1,3-Bis(2,2-dimethyl-3-aminopropyl)-benzene and Sebacyl Chloride

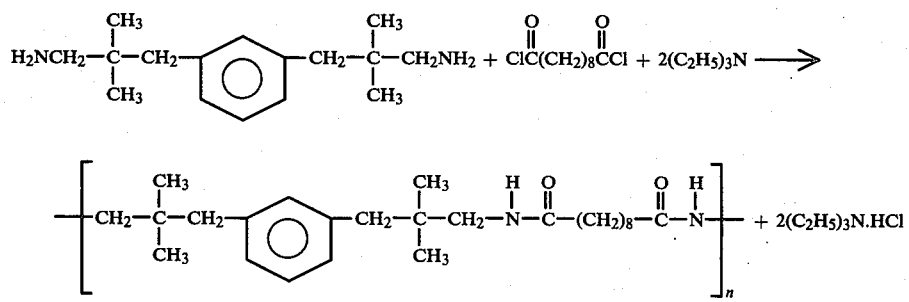

In a 300 ml flask, equipped with a paddle stirrer, a reflux condenser and a nitrogen bubbler, was put 4.00 g of 1,3-bis(2,2-dimethyl-3-aminopropyl)benzene, 5.00 ml of triethylamine, and 50 ml of chloroform which had been passed through basic alumina under nitrogen. With vigorous stirring, a solution of 3.85 g of sebacyl chloride (freshly distilled) in 25 ml of purified chloroform was added all at once. The mixture was stirred for 10 minutes and poured into 500 ml of hexane with stirring. Stirring was continued for a few minutes, the mixture was filtered, and the isolated solid was rinsed on the filter with hexane. The dried solid was washed in a blender once with 200 ml of water and once with 100 ml of acetone. The resulting sticky polymer was dried in a vacuum oven at room temperature and then washed in the blender three times with 200 ml of water. After being dried in a vacuum oven at 70°, the polymer weighted 3.20 g: inherent viscosity (0.05% in m-cresol at 25°)=0.36.

In a 50-ml, round-bottomed flask was placed 5.0 g of 1,3-bis(2,2-dimethyl-3-aminopropyl)benzene and 7.94 g of diphenyl bibenzoate. The flask was equipped as described in Example 13 and then heated in an oil bath at 210° to 220° with the nitrogen capillary positioned above the reaction mixture. Within 10 minutes, the charge completely melted whereupon the flask was agitated to insure thorough mixing of the reactants. After 3 hrs and 20 min of heating at 210° to 220°, the capillary was lowered so that nitrogen bubbled up through the still liquid reaction mixture, and the temperature of the oil bath was raised so that after 30 min its temperature was 265°. Heating at this temperature was continued for 2 hrs 45 min, during the final hour of which the reactor was evacuated with an oil pump (~0.5 mm). After the flask had cooled to room temperature under vacuum, the polymer was isolated: wt=9.2 g (100%). The polymer was ground up in a blender with 200 ml of water, reisolated by filtration, and finally dried in a vacuum oven at 70°. A clear, tough film was pressed at 220° and 500 lbs. The inherent viscosity (0.05% in m-cresol at 25°)=0.57.

EXAMPLE 19

A Polyamide from 1,4-Bis(2,2-dimethyl-3-aminopropyl)-tetramethylbenzene and Sebacyl Chloride

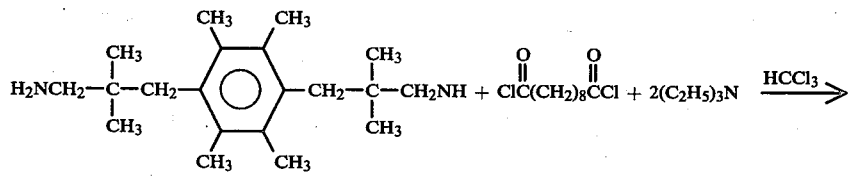

-continued

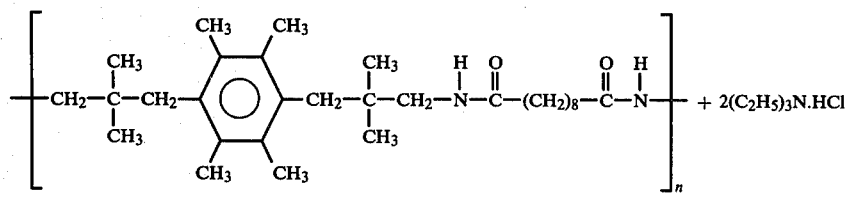

In a 1-liter flask, equipped with a paddle stirrer, a reflux condenser, and a nitrogen bubbler, was placed 10.00 g of 1,4-bis(2,2-dimethyl-3-aminopropyl)-tetramethylbenzene, 10.1 ml of triethylamine, and 125 ml of chloroform which had been passed through basic alumina under nitrogen. The reaction flask was cooled in a room-temperature water bath, and with vigorous stirring a solution of 7.85 g of freshly distilled sebacyl chloride in 50 ml of purified chloroform was added all at once. After the mixture had been stirred vigorously for another 30 minutes, 500 ml of hexane was added, and stirring was continued for 30 minutes. Then with stirring, 200 ml of water was added. Stirring was continued for a short time and the mixture was allowed to stand at room temperature overnight. The polymer was isolated by filtration, rinsed on the filter with water, and then washed in a blender once with 200 ml of water, once with 200 ml of acetone, and three times with 200 ml of water. The isolated polymer was dried overnight in a vacuum oven at 70°. There was thus obtained 9.50 g (61%) of product: inherent viscosity (0.05% in m-cresol at 25°)=0.38. A clear, colorless, brittle film was pressed at 180° and 500 lbs pressure.

EXAMPLE 20

A Polyamide from 3,3'-Bis(2,2-dimethyl-3-aminopropyl)-biphenyl and Sebacyl Chloride In a 250-ml flask equipped with a paddle stirrer, a reflux condenser, and a nitrogen bubbler was placed 5.03 g of 3,3'-bis(2,2-dimethyl-3-aminopropyl)-biphenyl, 4.8 ml of triethylamine and 75 ml of chloroform which had been passed through basic alumina under nitrogen. With vigorous stirring, a solution of 3.71 g of freshly distilled sebacyl chloride in 20 ml of purified chloroform was added all at once. The mixture was stirred for 30 min and then poured with stirring into 150 ml of hexane. As stirring was continued, the total volume was increased to 350 ml with hexane. The resulting precipitate was filtered, rinsed on the filter with hexane, and then washed in a blender successively with 100 ml of water, 100 ml of acetone, and finally three times with 100 ml of water. After being dried in a vacuum oven at 70° overnight, the polymer weighed 4.80 g (63%): inherent viscosity (0.05% in m-cresol at 25°)=0.64.

EXAMPLE 21

A Polyamide from 3,3'-Bis(2,2-dimethyl-3-aminopropyl)-biphenyl and Terephthaloyl Chloride

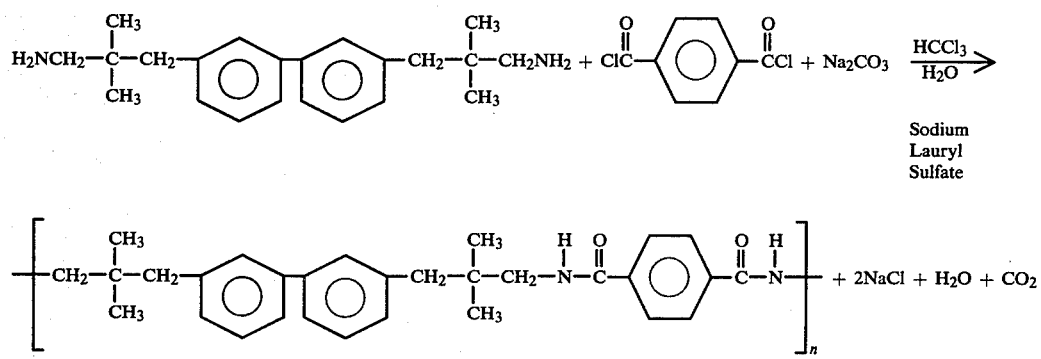

Sodium Lauryl Sulfate

In a 1-liter blender was put 100 ml of distilled water, 40 ml of chloroform (which had been passed through basic alumina), 0.77 g of sodium lauryl sulfate, 3.28 g of anhydrous sodium carbonate and 5.04 g of 3,3'-bis(2,2-dimethyl-3-aminopropyl)biphenyl. The mixture was stirred moderately fast until a uniform emulsion was

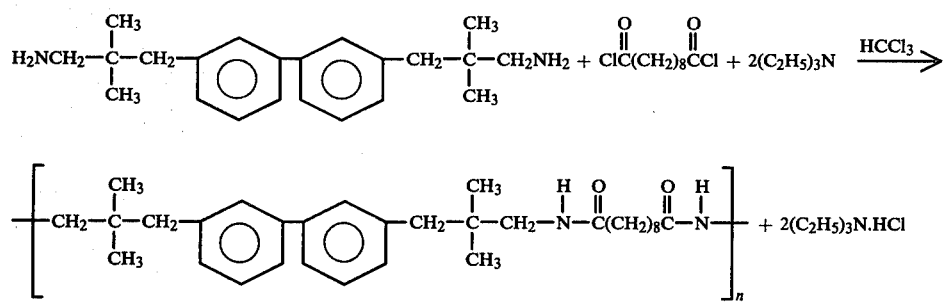

obtained. Then a solution of 3.15 g of terephthaloyl chloride in 110 ml of purified chloroform was added in a few seconds. The mixture was stirred for 14 minutes and then 300 ml of hexane was added. After a further 7 minutes of stirring, an additional 200 ml of hexane was added with stirring. In order to more completely coagulate the polymer, the mixture was added with stirring to dilute aqueous HCl. The resulting polymer was filtered, washed in a blender successively with 100 ml of water, 100 ml of water, and dried in a vacuum oven at 70°. There was thus obtained 2.76 g of colorless solid polymer: inherent viscosity (0.05% in m-cresol at 25%)=0.27.

EXAMPLE 22

A Polyamide from 3,3'-Bis-(2,2-dimethyl-3-aminopropyl)-biphenyl and Diphenyl Bibenzoate isolated: weight=8.2 g (~100%) of clear, amber-colored, tough solid: inherent viscosity (0.05% in m-cresol at 25°)=0.29.

Long tough fibers could be drawn from this polymer heated on a metal block at 300° to 310°. A clear, colorless, tough film was pressed at 220° and 500 lbs pressure.

EXAMPLE 23

A Polyamide from 3,3'-Bis(2,2-dimethyl-3-aminopropyl)-biphenyl and Diphenyl 2,6-Naphthalenedicarboxylate

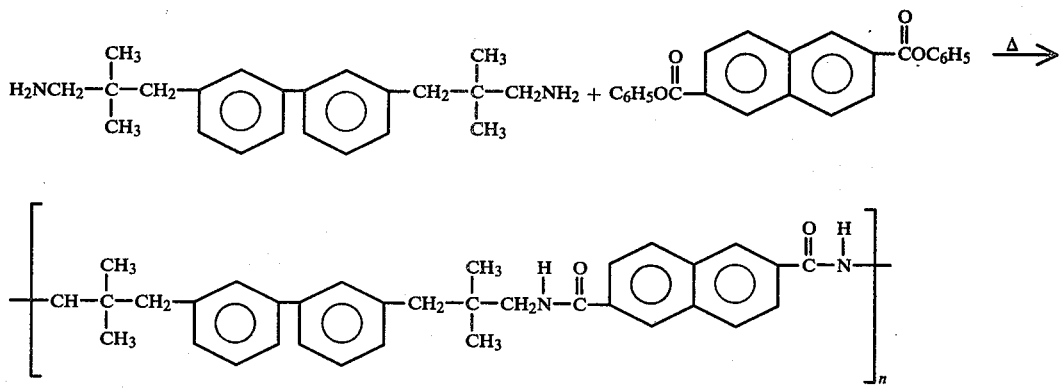

In a 50-ml flask was placed 5.05 g of 3,3'-bis(2,2-dimethyl-3-aminopropyl)biphenyl and 5.73 g of diphenyl 2,6-naphthalenedicarboxylate. The flask was then fitted as described in Example 12, and heated in an oil bath at 220°. After 10 minutes of heating, the charge became liquid whereupon the flask was agitated to insure complete mixing of the reactants. After 2 hr 30 min

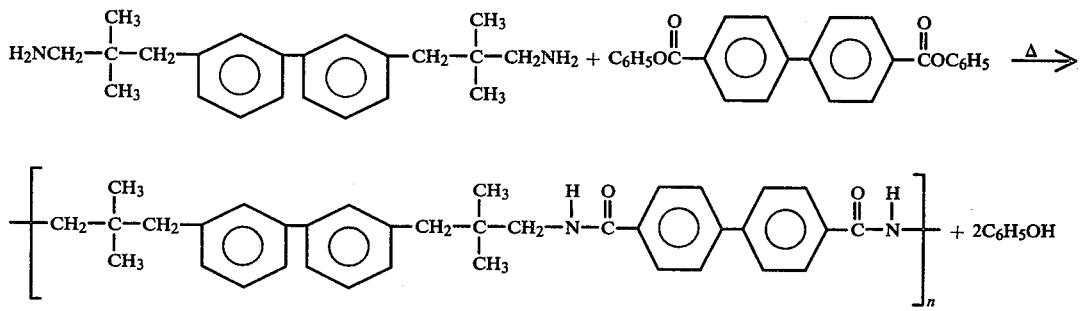

In a 50-ml round-bottomed flask was placed 5.05 g of 3,3'-bis(2,2-dimethyl-3-aminopropyl)biphenyl and 6.14 g of diphenyl bibenzoate. The flask was equipped as described in Example 13 and then heated for 30 minutes in an oil bath at about 220° with the nitrogen capillary positioned above the reaction mixture. The capillary was then lowered so that nitrogen bubbled up through the reaction mixture and the heating at 220° continued for about 4 hours. The bath was then heated more strongly so that its temperature rose to 270° in the next hour. Heating at 270° was continued for 1 hr 30 min. During the final hour of the heating period, the flask was evacuated with an oil pump. The flask was then removed from the oil bath and allowed to cool to room temperature. The flask was broken and the polymer was of heating at 220°, the temperature of the oil bath was increased so that after 43 min the temperature was 270°. The oil bath was maintained at this temperature for 2 hr 47 min, during the last 1 hr 30 min of which the system was evacuated at 0.20 mm. The reactor was allowed to cool under vacuum and the polymer was isolated, ground up in a blender with 200 ml of water, filtered and dried in a vacuum oven at 70°: wt=7.10 g (90%): inherent viscosity (0.05% in m-cresol at 25°)=1.08.

EXAMPLE 24

A Polyamide from 2,6-Bis(2,2-dimethyl-3-aminopropyl)-naphthalene and Diphenyl Terephthalate

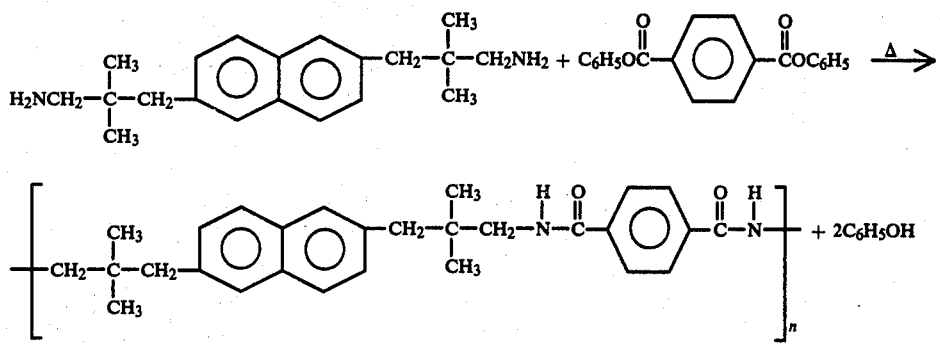

In a polymber tube (23 cm×2.5 cm), fitted with a side arm, was put 5.00 g of 2,6-bis(2,2-dimethyl-3-aminopropyl)naphthalene and 5.33 g of diphenyl terephthalate. A nitrogen capillary was positioned in the tube so that the end of the capillary was above the reaction mixture. The tube was lowered into the vapor of a 220° vapor bath and heated at that temperature for 4 hr 30 min. After 1 hr 15 min at 220°, the capillary was lowered so that the nitrogen bubbled up through the reaction mixture. The tube was then heated at 280° for 2 hrs 30 min. During the last 30 min of this heating, the tube was evacuated at about 2.5 mm. After the tube had cooled to room temperature, it was broken and 5.61 g (78%) of polymer was isolated: inherent viscosity (0.05% in m-cresol at 25°)=0.20.

EXAMPLE 25

A Polyamide from 4,4'-Bis(2,2-dimethyl-3-aminopropyl)biphenyl and Sebacyl Chloride

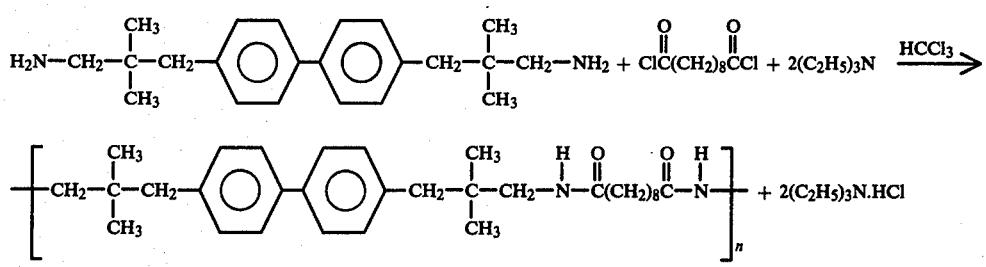

In a 300-ml flask, equipped as described in Example 20, was placed 5.00 g of 4,4'-bis(2,2-dimethyl-3-aminopropyl)biphenyl, 4,8 ml of triethylamine and 75 ml of chloroform which had been passed through basic alumina under nitrogen. With vigorous stirring, a solution of 3.68 g of freshly distilled sebacyl chloride in 125 ml of purified chloroform was added all at once. The mixture was stirred for 10 min and then poured into 500 ml of vigorously stirred hexane. The resulting precipitate was isolated by filtration, dried on the filter and washed in a blender once with 200 ml of water, once with 100 ml of acetone, and finally three times with 200 ml of water. After being dried in a vacuum oven at 70°, the polymer weighed 6.3 g (83%): inherent viscosity (0.05% in m-cresol at 25°)=0.46.

EXAMPLE 26

A Polyamide from 4,4'-Bis(2,2-dimethyl-3-aminopropyl)-biphenyl and Diphenyl Bibenzoate

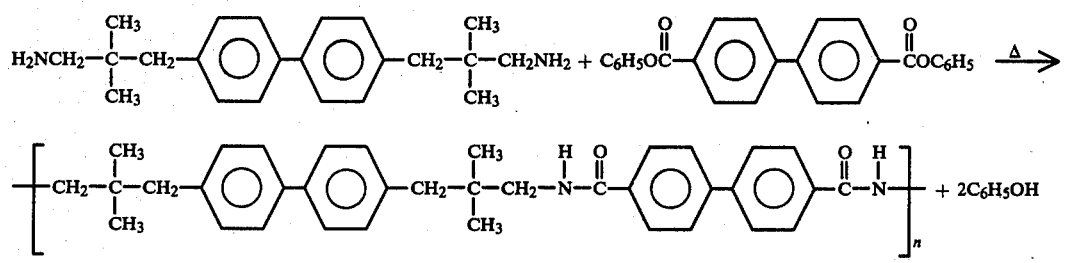

In a large test tube (30 cm×3.5 cm), fitted with a 2-hole rubber stopper containing a straight glass tube and a right angle glass tube, was put 4.0 g of 4,4'-bis(2,2-dimetyl-3-aminopropyl)biphenyl and 4.86 g of diphenyl bibenzoate. A nitrogen capillary was fitted into the straight tube and positioned so that its end was above the reaction mixture. The right angle tube was connected to a nitrogen bubbler. The test tube was lowered into the vapor of a 220° vapor bath and heated at that temperature for 3 hrs 45 min. The tube was then heated in a 280° vapor bath for 1 hr 25 min. During the last 40 minutes the tube was evacuated with an oil pump. After the tube had cooled to room temperature, 6.5 g (99%) of polymer was isolated. Successive washings of the polymer in a blender with 100 ml of water, 100 ml of acetone, and then 3 times with 100 ml of water and then drying in a vacuum oven at 70° gave 6.16 g of product: inherent viscosity (0.05% in sulfuric acid at 25°)=0.40.

EXAMPLE 27

Polyamide from 3,3'-Dichloro-4,4'-Bis(2,2-dimethyl-3-aminopropyl)-biphenyl and Diphenyl Bibenzoate When an equivalent amount of 3,3'-dichloro-4,4'-bis(2,2-dimethyl-3-aminopropyl)biphenyl is substituted for the 4,4'-bis(2,2-dimethyl-3-aminopropyl)-biphenyl in the procedure of Example 26, a polyamide with the repeating unit

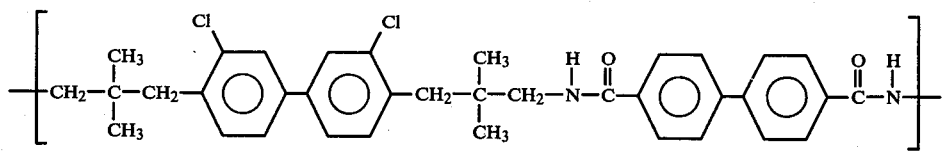

is formed.

COMPARATIVE EXAMPLES

These experiments were undertaken to compare the thermal stability of disclosed terephthalamide polymers which are derived from diamines having the formula

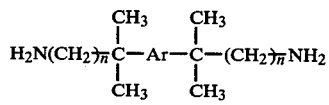

wherein n is 0, 1, 2 or 4, with the terephthalamide polymers derived from diamines of the present invention which are of the formula

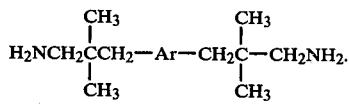

I. Preparation of 4,4'-Bis(1,1-dimethyl-3-aminopropyl)biphenyl

A. 4,4'-Bis(1,1-dimethyl-2-carboxyethyl)biphenyl

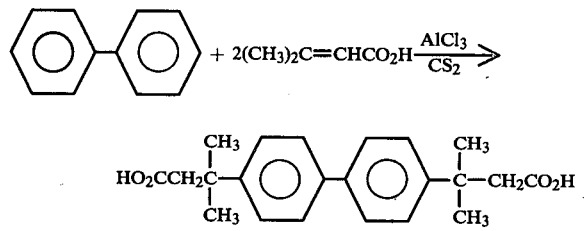

In a 1 liter flask equipped with a magnetic stirrer, a reflux condenser capped with a nitrogen bubbler, and an addition funnel was put 250 g of carbon disulfide, 23.1 g of biphenyl and 80 g of anhydrous aluminum chloride. To this stirred mixture, a solution of 30.0 g of β,β-dimethyl acrylic acid dissolved in 165 ml of carbon disulfide was added from the addition funnel in about ¼ hour. The resulting mixture was stirred at room temperature for 2 hours and then heated to gentle reflux for 1 hour. After being cooled to room temperature, the mixture was poured into 1 kilogram of chopped ice with vigorous stirring, and stirred for about 16 hours.

The resulting colorless solid was filtered, rinsed in the filter with water, and then stirred for a few minutes on a hot plate with a solution of 200 ml of concentrated aqueous ammonia in 200 ml of water. The resulting suspension was filtered to remove the alumina and the solid was rinsed on the filter with water. The combined filtrate and rinsings were cooled in an ice-water bath and with stirring were acidified with concentrated HCl until no more precipitation occurred. The resulting solid was isolated by filtration, rinsed on the filter with much water, and dried in a vacuum oven at 70°; wt: 36.3 g (68%), mp=145° to 220°. This material was dissolved in 375 ml of absolute ethanol at reflux, and the hot solution was filtered through a medium sintered glass filter and cooled to 10° C.

The resulting 4,4'-bis(1,1-dimethyl-2-carboxyethyl)-biphenyl, after isolation by filtration and drying, weighed 11.4 g and melted at 233.5° to 236.5°. An additional 3.75 g of product (mp=230° to 237°), was obtained by evaporating the filtrate to 150 ml. One more recrystallization from ethanol raised the melting point to 237° to 239°. Two further recrystallizations from o-dichlorobenzene at reflux (7.5 ml/gm) gave the product as essentially colorless crystals melting at 244.5° to 245°.

Anal. Calc'd for $C_{22}H_{26}O_4$: C, 74.55; H, 7.39. Found: C, 74.82; 75.12 H, 7.30; 7.28.

B. 4, 4'-Bis(1,1-dimethyl-2-amidoethyl)biphenyl

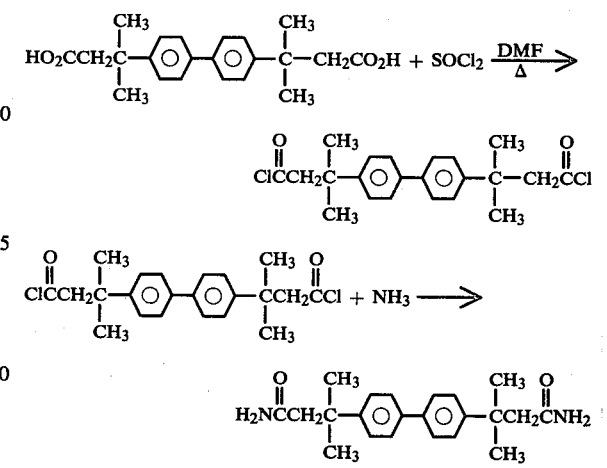

All equipment was dried at 135° before assembly and flushed with nitrogen after assembly. In a 200 ml flask equipped with a nitrogen stirrer, and a reflux condenser capped with a nitrogen bubbler was put 20 g of 4,4'-bis- (1,1-dimethyl-2-carboxyethyl)biphenyl, 60 ml of thionyl chloride and 2 drops of anhydrous dimethylformamide. This mixture was refluxed for 16 hours. The excess thionyl chloride was distilled off on the water pump and the resulting solid residue freed of the last trace of thionyl chloride by evacuation on the oil pump (~0.10 mm) at room temperature. There was thus obtained 23.08 g of 4,4'-bis(1,1-dimethyl-2-chlorocarbonylethyl)biphenyl as an almost colorless crystalline solid.

All of this product was dissolved in 750 ml of anhydrous tetrahydrofuran contained in a 2-liter flask fitted with a magnetic stirrer, a gas inlet tube which extended below the surface of the solution, and a reflux condenser capped with a nitrogen bubbler. While the mixture was stirred, anhydrous ammonia was passed through the gas inlet tube until no more precipitation was evident (1½ hours). The resulting mixture was filtered and the filter cake was rinsed with a little tetrahydrofuran. After the filter cake had been dried on the filter, it was stirred for ¼ hour with 500 ml of water. The mixture was filtered and the solid was rinsed on the filter with water. After drying in a vacuum oven at 70°, there was obtained 16.6 g (83%) of 4,4'-bis(1,1-dimethyl-2-amidoethyl)biphenyl melting at 207° to 209°. After two recrystallizations from ethanol (181 ml/gm), the product was obtained as colorless plates melting at 214.5° to 215.5°.

Anal. Calc'd. for $C_{22}H_{28}N_2O_2$: C, 74.96; H, 8.01; N, 7.95. Found: C, 75.55; 75.51; H, 7.79; 7.87; N, 7.43; 7.57. Further recrystallization of other batches gave product melting at 215.7° to 216.7°.

C. 4,4'-Bis(1,1-dimethyl-3-aminopropyl)biphenyl had been passed through acid alumina under nitrogen directly into the reaction vessel. With stirring at room temperature, 500 ml of a 25% solution of diisobutylaluminum hydride in toluene was added from the dropping funnel in ½-1 hour. The mixture was then refluxed for about 16 hours. After the mixture had been cooled in an ice-water bath, a solution of 30 ml of water in 140 ml of methanol was added dropwise with stirring during 55 minutes. This was followed by the dropwise addition of a solution of 140 ml of water in 280 ml of methanol during 25 minutes.

The resulting mixture was stirred for two hours at ice-bath temperature and for an additional hour at room temperature. The mixture was filtered under nitrogen, the solid was washed thoroughly on the filter with toluene, and the combined filtrates and washings were distilled on the water pump. The resulting solid residue was dried on the oil pump at room temperature to remove the last traces of solvent. This residue was then sublimed at 160° to 180°/0.1 mm to give 15 g (65%) of 4,4'-bis(1,1-dimethyl-3-aminopropyl)biphenyl as a colorless crystalline solid. Another sample prepared in the same manner was analyzed:

Anal. Calc'd for $C_{22}H_{32}N_2$: C, 81.42; H, 9.94; N, 8.63. Found: C, 80.89; 80.69; H, 10.03; 10.06; N, 7.89; 8.15.
The infrared spectrum of this material contains bands at 2.98μ and 3.04μ (—NH₂), 3.37μ and 3.47μ (saturated CH), 3.28μ (═CH), 6.32μ (NH₂ deformation and/or aromatic C═C), 6.66μ (aromatic C═C) and 12.13μ (p-disubstituted aromatic).

II. A Polyamide from 4,4'-Bis(1,1-dimethyl-3-aminopropyl)biphenyl and Diphenyl Terephthalate

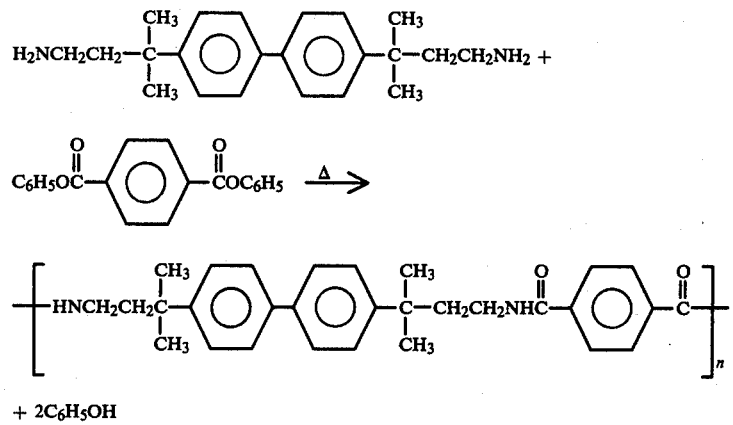

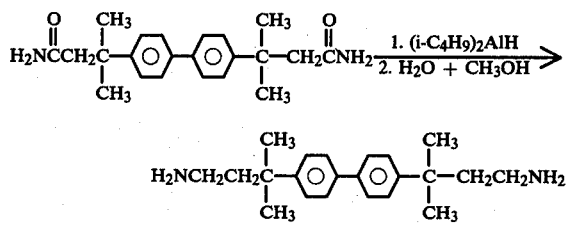

All equipment was dried at 135° before assembly and flushed with nitrogen after assembly. In a five-liter flask equipped with a magnetic stirrer, a dropping funnel, and a reflux condenser capped with a nitrogen bubbler, was put 25.00 g of 4,4'-bis(1,1-dimethyl-2-amidoethyl)biphenyl and 1250 ml of reagent grade toluene which All equipment was dried at 135° and let cool in a nitrogen dry box. The loading was also done in a nitrogen dry box. In a 100-ml flask was put 6.8652 g of 4,4'-bis(1,1-dimethyl-3-aminopropyl)biphenyl and 6.7342 g of diphenyl terephthalate (weight ratio of 1.01945, molar ratio of 1.0000). The reactants were thoroughly mixed and the flask was fitted with a 15 cm extension tube and a short path still head which had a small motor driven paddle stirrer inserted into it reaching to the bottom of the flask, and a small round bottomed flask as a receiver. The assembled set-up was connected to a nitrogen bubbler and the flask was inserted into an oil bath heated to approximately 220°. The reaction mixture was then submitted to the following heating, stirring and evacuation schedule:

| Oil Bath Temperature | |
|---|---|
| 218° to 224° | 40 min - stirred during last 37 min. |
| 224° to 232° | 16 hr 40 min |
| 232° to 268° | 1 hr 22 min |
| 268° to 270° | 4 hr 15 min |
| 270° to 263° | 2 hr 55 min - evacuated at 0.10 mm. |

The reactor was then allowed to cool under vacuum and the polymer was isolated. It weighed 9.5 g (99%). The polymer was ground in a micro mill sufficient to pass through a 40 mesh screen. It was then dried at 200° in a vacuum oven for about 16 hours. The inherent viscosity (0.25% in m-cresol at 25°)=0.42.

III. A Polyamide From 4,4'-Bis(2,2-dimethyl-3-aminopropyl)biphenyl and Diphenyl Terephthalate

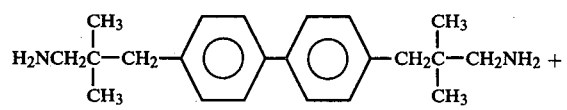

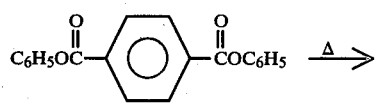

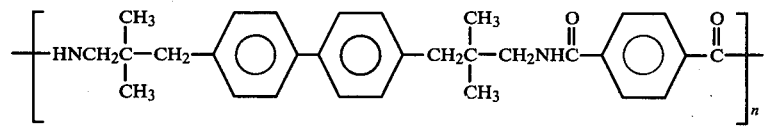

+ 2C₆H₅OH

In the same set-up described in Part II, a mixture of 9.6500 of 4,4'-bis(2,2-dimethyl-3-aminopropyl)biphenyl and 9.4659 g of diphenyl terephthalate (weight ratio of 1.01945, molar ratio of 1.0000) was submitted to the following heating, stirring and evacuation schedule:

| Oil Bath Temperature | |
|---|---|
| 210° to 220° | 1 hr 2 min - stirred |
| 220° | 1 hr 7 min |
| 220° to 300° | 1 hr 25 min |
| 300° | 2 hr 10 min |
| 300° | 1 hr - evaluated at 0.2 mm |

The polymer was isolated, broken up in blender with 300 ml of water, filtered, and then dried at 70° in the vacuum oven: wt=12.70 g (93%). The sample was then ground up in Wiley Mill sufficient to pass through a 20 mesh screen. It was then dried at 200° in a vacuum oven for about 16 hours. The inherent viscosity (0.25% in m-cresol at 25°)=0.49.

IV. Comparison of Thermal Stabilities of the Terephthalamides Derived From 4,4'-Bis(1,1-dimethyl-3-aminopropyl)biphenyl and 4,4'-Bis(2,2-dimethyl-3-aminopropyl)biphenyl Samples of the above polymers of comparable inherent viscosities were subjected to isothermal thermogravimetric analyses (TGA) under nitrogen using a Du Pont Thermo Gravimetric Analyzer Model 990-951. This established technique measures decomposition via weight loss. The test results are tabulated below.

| | Comparative Thermal Stabilities | | |
|---|---|---|---|
| | % Weight Loss After One Hour | | (A − B) × 100 |
| Temperature | A | B | B |
| 300° | 2.5% | 1.3% | 92.3% |
| 350° | 8.7% | 4.2% | 107.1% |
| 375° | 26.5% | 17.5% | 51.4% |

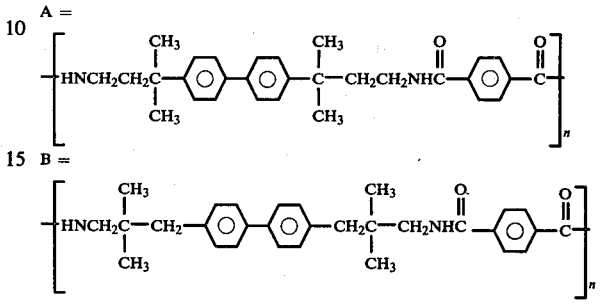

The data show that in the temperature range 300° to 375° C., polyamide A loses 50% to 107% more weight by thermal decomposition than does polyamide B. Polymer A was semimolten and collapsed and polymer B was molten at 300° C. Both polymers were molten at 350° C. and 375° C. Thus, the difference in size of the original particles cannot effect the thermal decomposition test results.

We claim:

1. Thermally stable, rigid polyamide having a repeating unit of the formula

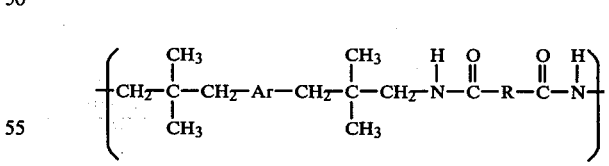

in which Ar is arylene selected from the group consisting of 1,2-phenylene, 1,3-phenylene, 1,4-phenylene, 2,2'-biphenylene, 3,3'-biphenylene, 4,4'-biphenylene and 2,6-naphthylene, said arylene being unsubstituted or substituted with methyl or chloro, and R is Ar, alkylene of 1 to 20 carbon atoms, or oxygen-interrupted alkylene of 3 to 20 carbon atoms.

2. The polymer of claim 1 in which R is Ar.

3. The polyamide of claim 1 in which Ar is an unsubstituted arylene and R is an alkylene of 1 to 20 carbon atoms.

* * * * *

UNITED STATES PATENT AND TRADEMARK OFFICE
CERTIFICATE OF CORRECTION

PATENT NO. : 4,451,642
DATED : May 29, 1984
INVENTOR(S) : August H. Frazer and John F. Harris, Jr.

It is certified that error appears in the above—identified patent and that said Letters Patent is hereby corrected as shown below:

At column 11, line 38, "0.16 g" should read --9.16 g--.

Column 31, line 10, delete "water" and substitute therefor --acetone, and then three times with 100 ml of water, --.

Signed and Sealed this

Twenty-sixth Day of February 1985

[SEAL]

Attest:

DONALD J. QUIGG

Attesting Officer

Acting Commissioner of Patents and Trademarks